US010324037B2

(12) United States Patent
Hudson

(10) Patent No.: US 10,324,037 B2
(45) Date of Patent: Jun. 18, 2019

(54) LOW ENERGY LASER SPECTROSCOPY LELS

(71) Applicant: Gustav Hudson, Fallbrook, CA (US)

(72) Inventor: Gustav Hudson, Fallbrook, CA (US)

( * ) Notice: Subject to any disclaimer, the term of this patent is extended or adjusted under 35 U.S.C. 154(b) by 132 days.

(21) Appl. No.: 14/559,744

(22) Filed: Dec. 3, 2014

(65) Prior Publication Data

US 2016/0161411 A1    Jun. 9, 2016

Related U.S. Application Data

(60) Provisional application No. 61/903,395, filed on Nov. 13, 2013.

(51) Int. Cl.
| | | |
|---|---|---|
| *H01S 5/06* | (2006.01) | |
| *H01S 5/34* | (2006.01) | |
| *G01N 21/65* | (2006.01) | |

(52) U.S. Cl.
CPC ........... *G01N 21/65* (2013.01); *H01S 5/0615* (2013.01); *G01N 21/658* (2013.01); *G01N 2021/653* (2013.01); *G01N 2021/656* (2013.01); *G01N 2201/0612* (2013.01); *H01S 5/3416* (2013.01)

(58) Field of Classification Search
CPC .................. G01N 21/65; H01S 5/34
See application file for complete search history.

(56) References Cited

U.S. PATENT DOCUMENTS

| | | | | |
|---|---|---|---|---|
| 3,953,809 A | * | 4/1976 | Kawamoto | ............ H01S 5/042 372/26 |
| 4,439,861 A | * | 3/1984 | Bradford | ............... H01S 3/1022 372/25 |

(Continued)

OTHER PUBLICATIONS

Wang, Yun. "Observational probes of dark energy." arXiv preprint arXiv:1201.2110 (2012).*

(Continued)

*Primary Examiner* — Shawn Decenzo
*Assistant Examiner* — Rufus L Phillips
(74) *Attorney, Agent, or Firm* — Continuum Law; Robert P. Cogan

(57) ABSTRACT

An extremely sensitive spectroscopy method utilizes a laser modified to an extremely low emission with an integrated control system, interfaced within a typical Raman platform to comprise low energy laser spectroscopy (LELS). LELS acquires and utilizes a quantum entangled state of photons and particles, including omnipresent cosmological dark matter particles (OCDM) and omnipresent cosmological dark energy (OCDE). The OCDM and OCDE matter has an affinity to particles of same OCDM and OCDE matter in target specimens, with same-time data results of high sensitivity. In a semiconductor light emitter, electron flow at a low energy level is provided to a quantum well to produce a quantum tunneling of electrons into an active region of the laser quantum well and creating sublasering. Sublasering allows OCDM and OCDE to become entangled with other particles and energies in the laser's quantum well and create a transmission package comprising quantum entangled fields, waves, wave packages, states and energies. Providing a triggering pulse causes a second tunneling, carrying the transmission package for emission.

8 Claims, 15 Drawing Sheets

(56) References Cited

U.S. PATENT DOCUMENTS

| | | | | |
|---|---|---|---|---|
| 4,695,857 A * | 9/1987 | Baba | ............... | B82Y 20/00 148/DIG. 160 |
| 4,882,734 A * | 11/1989 | Scifres | ............... | B82Y 20/00 372/45.012 |
| 5,213,998 A * | 5/1993 | Qiu | ............... | B82Y 20/00 117/108 |
| 5,300,066 A * | 4/1994 | Manoukian | ............... | A61B 18/24 606/15 |
| 5,303,710 A * | 4/1994 | Bashkansky | ............... | G01N 21/65 356/301 |
| 5,534,997 A * | 7/1996 | Schrader | ............... | G01N 21/65 356/301 |
| 5,621,522 A * | 4/1997 | Ewing | ............... | G01N 21/65 356/301 |
| 6,593,589 B1 * | 7/2003 | Osinski | ............... | B82Y 10/00 257/22 |
| 6,724,013 B2 * | 4/2004 | Kneissl | ............... | H01S 5/34333 257/13 |
| 2003/0122561 A1 * | 7/2003 | Stokes | ............... | G01N 21/66 324/762.07 |
| 2003/0141459 A1 * | 7/2003 | Hegazi | ............... | G01N 21/6408 250/461.1 |
| 2005/0171433 A1 * | 8/2005 | Boppart | ............... | A61B 5/416 600/473 |
| 2007/0019208 A1 * | 1/2007 | Toida | ............... | A61B 5/0066 356/511 |
| 2007/0280303 A1 * | 12/2007 | Koch | ............... | B82Y 20/00 372/4 |
| 2011/0261354 A1 * | 10/2011 | Sinfield | ............... | G01J 3/02 356/301 |
| 2014/0031649 A1 * | 1/2014 | Nakao | ............... | A61B 5/1455 600/322 |
| 2014/0050242 A1 * | 2/2014 | Taylor | ............... | H01L 29/0688 372/45.012 |

OTHER PUBLICATIONS

Yan, Ping, et al. "Laser performance of monolithic Cr, Nd: YAG crystal with prepumping modulation." Optical Engineering 44.1 (2005): 014201-014201.*

Coldren, Larry A., and Scott W. Corzine. "Diode lasers and photonic integrated circuits." Second Edition; Wiley;2012.*

* cited by examiner

FIG. 2G

| | |
|---|---|
| Filename: | Acquisition |
| Date and Time: | Fri Oct 28 15:01:05 2011 |
| Software Version: | |
| Temperature (C): | -15 |
| Model: | |
| Data Type: | Counts |
| Acquisition Mode: | Accumulate |
| Trigger Mode: | External |
| Exposure Time (secs): | 0.035 |
| Number of Accumulations: | 100 |
| Readout Mode: | Full Vertical Binning |
| Vertical Shift Speed (usecs): | 16 |
| Pixel Readout Time (usecs): | 16 |
| Serial Number: | |
| Intelligate: | off |
| Insertion delay: | ultra fast |
| Gain level: | 20 |
| Integrate on chip: | off |
| Gate Mode: | Fire only |
| Gate Width (nsecs): | 0.2 |
| Gate Delay (nsecs): | 0.3 |
| Wavelength (nm): | 540.085 |
| Grating Groove Density (1/mm): | 1200 |
| Grating Blaze: | 500 |
| Spurious Noise Filter Mode: | No Filter |
| Photon counted: | false |
| Data Averaging Filter Mode: | No Filter |

LOW ENERGY LASER SPECTROSCOPY LELS

CROSS-REFERENCE TO RELATED APPLICATIONS

This application claims priority from provisional application Ser. No. 61/903,395 entitled "Low Energy Laser Spectroscopy LELS" and filed on Nov. 11, 2013. The contents of this provisional application are fully incorporated herein by reference.

FIELD

The present subject matter relates to spectroscopy, e.g., laser Raman spectroscopy, in general and more particularly to irradiation of samples by gentle low energy and generation of spectra of energies returned from the irradiated samples.

BACKGROUND

Prior forms of spectroscopy have used relatively high levels of energy to induce radiation by a sample. This has left unresolved problems in many different applications.

For example, there have been innovative oncology discoveries using fluorescent dyes and bio tags to target tumor sites. Some of the chemicals used in lab research and the use of high energy lasers are not conducive for in vivo human tissue study. Further, the necessity of a less invasive tumor biopsy device is preferable as needle biopsy of a cancerous tumor may risk dispersion of cancerous cells from the sample site upon withdrawal of the biopsy needle from a target tumor specimen.

SUMMARY

In accordance with the present subject matter, use is made of particles with unusual properties that have been found. The low energy laser method allows for omnipresent cosmological dark matter particles (OCDM) and omnipresent cosmological dark energy (OCDE) to become entangled with other particles and energies in the laser's quantum well. The quantum entangled fields, waves, wave packages, states and energies and are carried along to laser emission. The OCDM, defined by its properties on spectral display, has a natural affinity to OCDM omnipresent in all molecules and in the bonds around molecules. The OCDM has the capability of quantum tunneling, sampling specimen data, collecting specimen excitation data, and same time reemission back through the tunnel created.

After reemission to the spectrometer, the resulting spectra display a temporal delay. The irradiated entangled particle energies increase incrementally for many minutes after excitation. The low energy laser spectroscopy (LELS) spectroscopic method has extreme sensitivity and noiseless spectra using a single strand fiber optic for both emission to and reemission from an irradiated target specimen. This spectroscopic method may also use a long laser convergence, exclusive to LELS, increasing its usefulness for medical and many other spectroscopic arts.

DRAWINGS

The objects and features of the invention can be better understood with reference to the drawings and spectra described below, and in the claims. The drawings are not necessarily to scale, emphasis instead generally being placed upon illustrating the principles of the invention. In the drawings and spectra, like numerals are used to indicate like parts throughout the various views.

FIG. 1 is a block diagram of a low energy laser spectroscopy system constructed in accordance with the present subject matter;

FIG. 2 consists of FIGS. 2A through 2G, wherein FIG. 2A is a cross-sectional illustration of a Raman probe which both excites and collects energy from a specimen sample;

Figure 3A:
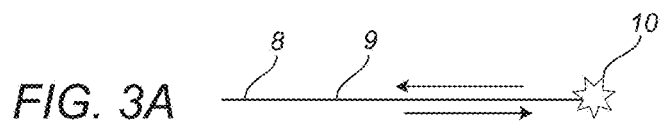
Figure 3B:
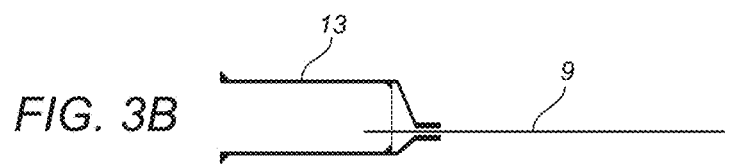
Figure 3C:
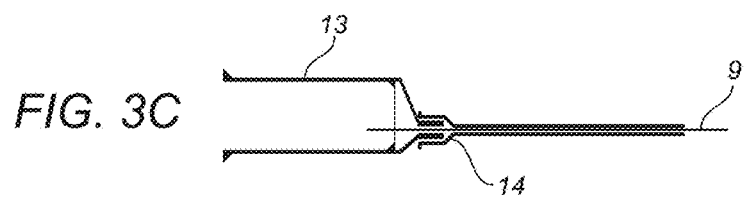
Figure 3D:
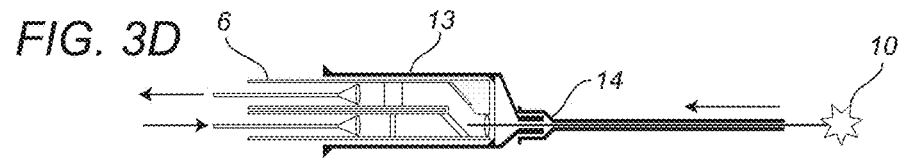
Figure 3E:
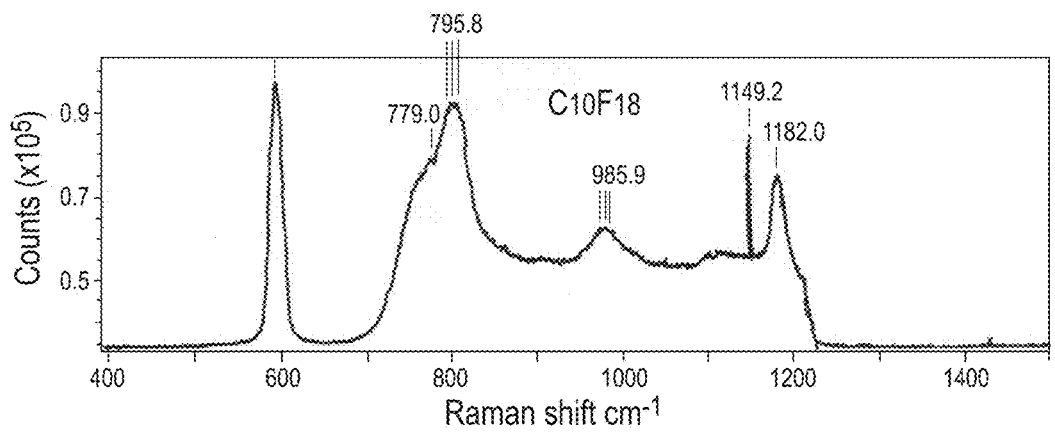
Figure 4A:
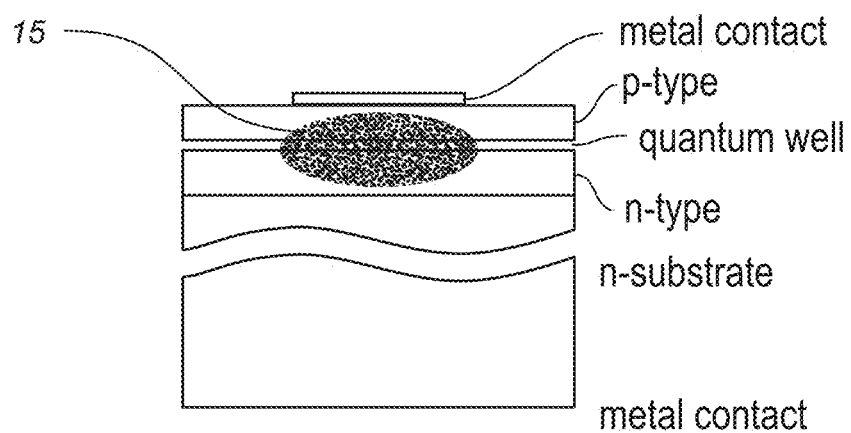
Figure 4B:
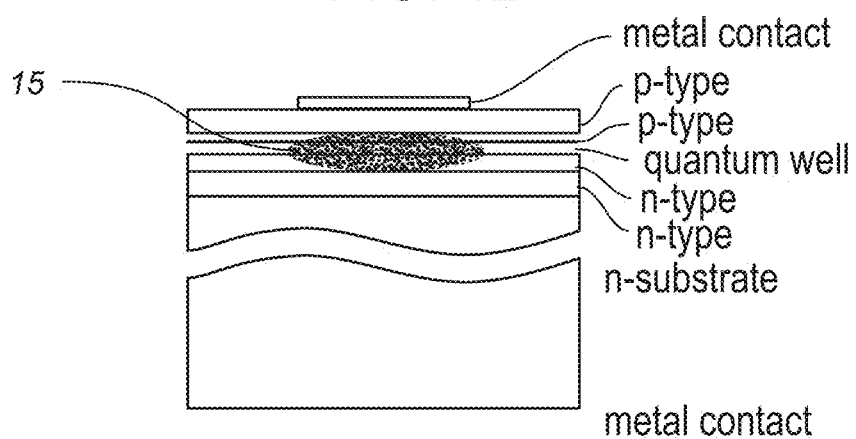
Figure 5A:
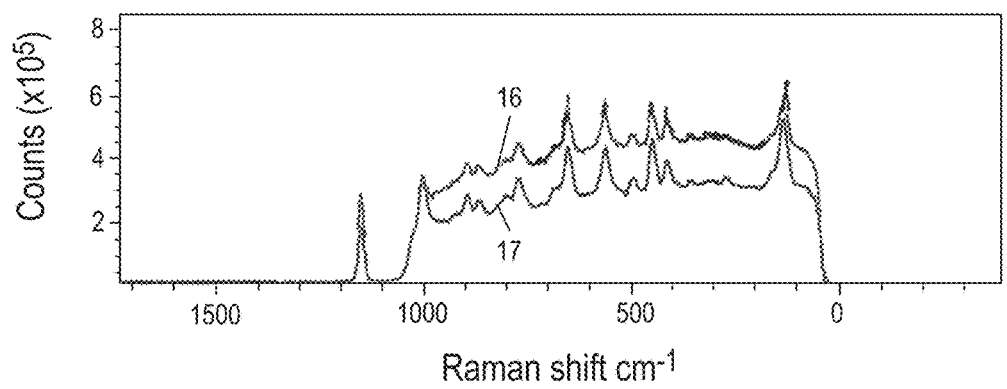
Figure 5B:
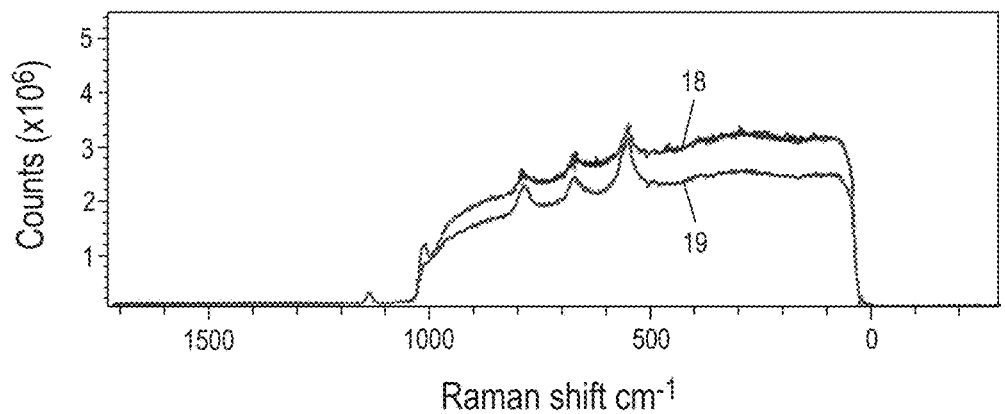
Figure 7A:
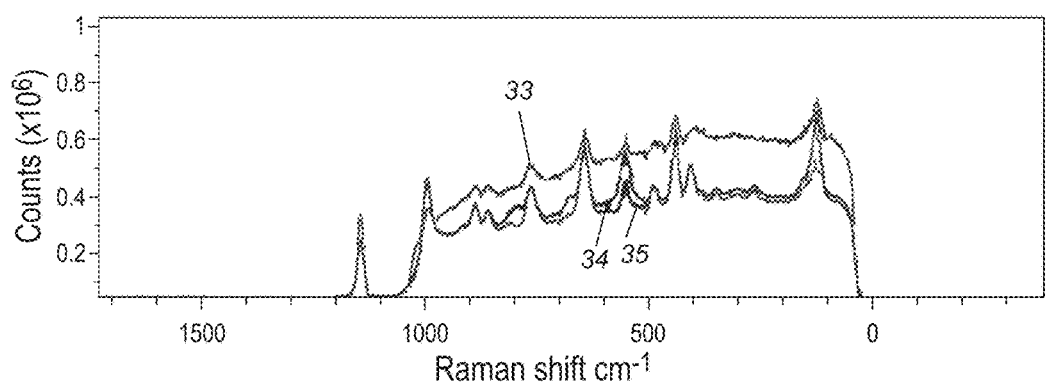
Figure 7B:
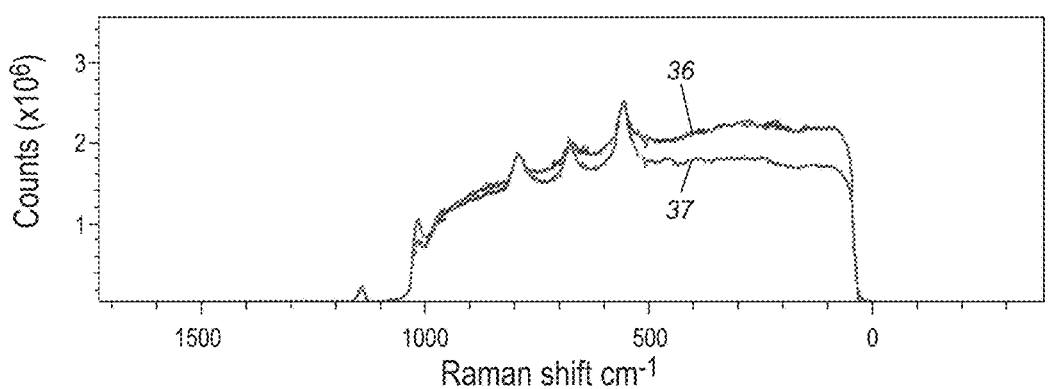
Figure 7C:
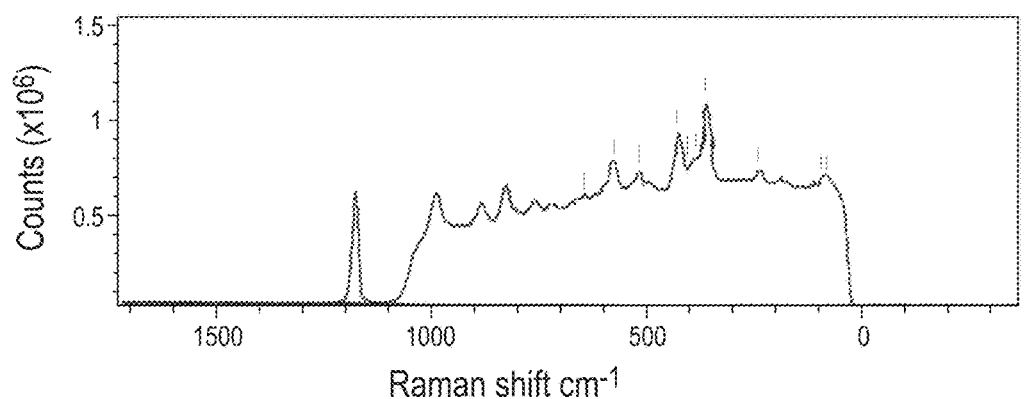
Figure 7D:
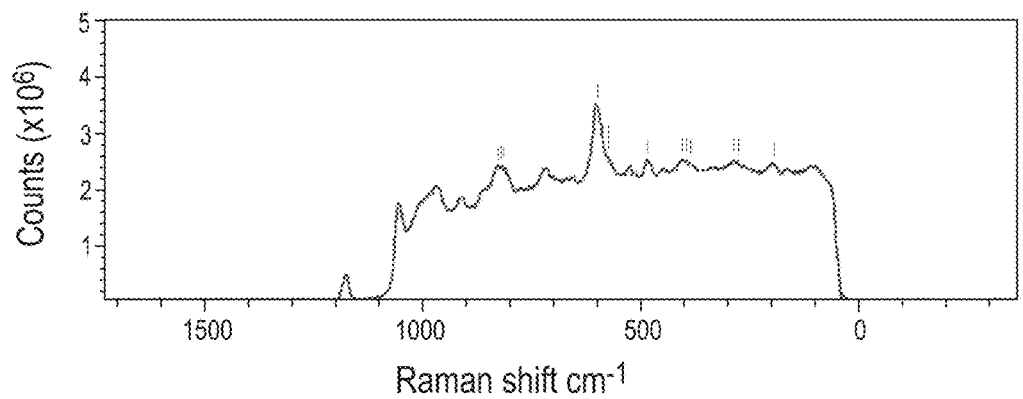
Figure 7E:
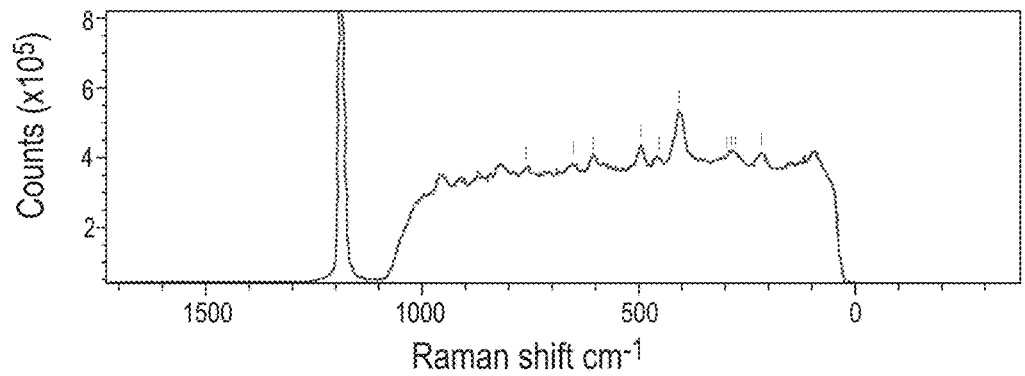

FIG. 3 consists of FIGS. 3A through 3E, wherein FIG. 3A is a cross-sectional illustration of a single fiber-optic strand which is included in a bio probe;

FIG. 3B is a cross-sectional illustration of the single fiber optic strand of FIG. 3A inserted into a syringe;

FIG. 3C is a cross-sectional illustration of the syringe of FIG. 3B with a needle affixed into the bio probe with the fiber-optic strand pre-inserted;

FIG. 3D is a cross-sectional illustration of the syringe and needle assembly of FIG. 3C housing a Raman probe;

FIG. 3E is a plot of spectral data received by the Raman probe of FIG. 3D from an in vivo specimen;

FIG. 4 consists of FIGS. 4A and 4B, wherein FIG. 4A is a diagram of one form of quantum well laser diode suitable for use in the present Raman probe;

FIG. 4B illustrates a further form of laser diode comprising a separate confinement laser quantum well;

In FIG. 5, consisting of FIGS. 5A and 5B, wherein FIG. 5A comprises spectrum plots of aspirin and of cetirizine as irradiated through a blister pack container;

FIG. 5B comprises spectrum plots of aspirin and of cetirizine preparation removed from the blister pack;

FIG. 6 consists of FIGS. 6A through 6E, each of which represents a spectrum for a different composition;

FIG. 7 consists of FIGS. 7A through 7E, wherein FIGS. 7A and 7B each represents a spectrum of one brand-name tablet and one counterfeit tablet and wherein FIGS. 7C through 7E each represent a spectrum for a respective brand-name medication;

FIG. 8 consists of FIGS. 8A through 8F, each representing the spectrum of a respective mineral or gemstone; and FIG. 9 consists of FIGS. 9A through 9D, each representing a spectrum of samples each containing a noble metal.

DESCRIPTION

An unusual and extremely sensitive form of spectroscopy uses a laser modified to an extremely low emission with external trigger command. In one preferred form, the modified laser is interfaced within a typical Raman platform which utilizes the capabilities of optics and electronics as a unit, thus creating low energy laser spectroscopy (LELS). LELS spectroscopy acquires a quantum entangled state of photons and particles, among which are those particles which are known to constitute approximately 93% of all matter in the universe, namely omnipresent cosmological dark matter particles (OCDM) and omnipresent cosmological dark energy (OCDE). The demonstrable behavior of OCDM and OCDE in nano scale as used by LELS holds universally true as OCDM and OCDE's macro scale behavior do in the cosmos as accepted by leading cosmologists' writings. Among the unique attributes of LELS methodology is a novel long length laser convergence extended single strand fiber optic probe which simultaneously emits and collects energies.

OCDM and OCDE acquisition opens new fields of science, chemistry and physics, and applications in medical, oncology, bio, food and pharmaceutical safety, chemical, and pathogen detection. LELS also detects counterfeit drug, currency, and fine art forgery; it has uses in mineral assay, crystal identification, precious gem authentication and identification. LELS also is capable of illicit drug and hazardous material detection, explosives detection, and secure uses for communications, cryptography, cosmology, astrophysics, propulsion, teleportation, and transportation. LELS spectroscopy has uses in pharmacology, biophysics, biochemistry, biotechnology, engineering, quantum computing, astrophysics, particle physics, optical sciences, communications and manufacturing.

Many applications have been found and more are possible from this novel discovery and inexpensive method of acquisition of OCDM and OCDE. The method of acquisition and the products of the method of acquisition of the quantum entangled states, fields, waves, wave packages, and energies as acquired by the LELS method are novel, exclusive and show a proven temporal delay in the spectroscopic display. The spectral count increases incrementally upon subsequent readings of the same spectral sample many minutes after initial excitation, evidencing a continued propagation of energy.

LELS is a spectroscopy method of novel and diverse uses. LELS was initially used for non-destructive laser spectroscopy developed for in vivo tumor tissue studies which is non-invasive to a tumor. This embodiment uses carbon fluorine, CF, one of the strongest bonds used to identify bio markers, bio tags and reagents. CF is a United States Food and Drug Administration (FDA) accepted compound used in some chemotherapy solutions. The success of creating the gentle-low energy laser method for medical diagnostics and other uses was accomplished with diligent R&D and testing. It has been shown much interest in the cancer research arena. The medical community's interest in acquiring this device demonstrates that LELS is a significant contribution to gentle, safe and fast oncology diagnosis and treatment. The method and device acquire and utilize unknown particles which may include OCDM and OCDE together with photons, electrons, particles, waves, wave packages, fields and energies in quantum entanglement. The laser produces a low energy excitation in the quantum well region. The electron flow to the N-P semiconductor produces a quantum tunneling of electrons into the active region of the laser quantum well creating a sub lasering low energy level, acquisition and propagation of particles, photons, electrons, OCDM and OCDE energies and waves within a quantum entangled state. The paired states are energetically favored, and electrons go in and out of those states preferentially.

The demonstrable behaviors of OCDM and OCDE on a nano scale hold universally true as OCDM and OCDE's observed attributes in macro scale in the cosmos. Many heretofore impossible scientific and physics uses may come of this discovery and invention. Secure communications and a non-decoherent quantum computer may be developed from the acquisition (ODMP) and OCDE, as the quantum particle duality in combination with time differential enables information to be transferred securely in same time increments or stored in time with complete security for future retrieval. Applications for use of OCDM and OCDE have not been fully explored, and are only now found with LELS method and invention, although through diligent R&D.

It has become clear that OCDM and OCDE may be acquired by many other means claimed here; through laser emissions, diode emissions, quantum tunneling, acoustics, electronic pulse, oscillation, spectroscopy of all types, Raman spectroscopy, stokes, antistokes, scalar field, scalar wave, microscopy, optical generating, optical signals, optical pulses, semiconductor, super cooled semiconductors, manipulation of photons, manipulation of particles, material excited by excitation fields, superposition, super symmetry, signal beam, wave energies, wave packages, solar and magnetic activity, unknown particles and fields, unknown waves, wave packages, wave energies, harmonic frequencies, vibrational energies, holographic display, atmospheric audio and spectral display, atomic and sub atomic particles, supercooled atomic and subatomic particles, and particle duality states, for the acquisition or use of OCDM and OCDE.

LELS invention has been particularly shown and described with reference to specific embodiments, it should be understood by those skilled in the art that various changes may be made thereto within the spirit and scope of the invention. The acquisition and method of acquisition of OCDM and OCDE findings and LELS in any of its possible configurations is an invaluable medical, technical, industrial and scientific resource. The relevant teachings of all the references, patents and patent applications cited are incorporated herein by reference in their entirety.

In some variations of the LELS method, the single strand longer length LELS probe method may be adapted for same-time multiple array sampling for pharmaceutical and many other scientific and commercial tests, an extended single strand fiber optic probe which simultaneously emits and collects energies. LELS uses exclusive pre-tested bio-organic, biomedical, cellular and chemical tags and markers and reagents. The method of acquisition and the products of the method of acquisition of the quantum entangled states, fields, waves, wave packages, and energies as acquired by the LELS method are novel, exclusive and show a proven temporal delay in the spectroscopic display.

The spectral count increases incrementally upon subsequent readings of the same spectral sample many minutes after initial excitation, evidencing continued propagation of energy. The LELS temporal delay effect has been observed and verified on spectral display from nanoseconds to many minutes long. These novel scientific and commercial discoveries and uses are possible which were only conceptualized heretofore. The LELS quantum energy emission and collection analyzes and quantifies the data of liquids, gasses, and solids without prior preparation. The same quantum emission tunnels through pharmaceutical packaging, solid pharmaceutical tablets and other solids without prior preparation.

LELS practical applications include a nondestructive low energy medical biopsy and collections probe, advancing oncological research and therapeutic uses by years. LELS method advances pharmaceutical, biological, chemical, mineral and hazardous material identification in real time, with simultaneous multiple sampling and remote sampling capabilities. LELS evidences exclusive same-time detection of bioorganic, biomedical, cellular and chemical tags and markers. LELS utilizes extremely sensitive counterfeit pharmaceutical and currency detection capability, and geological, metallurgical, gemological assay and verification. The low energy device has reliable unique properties, extreme sensitivity, diversity and functionality for many uses and yet to be explored uses. LELS method of sample detection and assay is inexpensive to acquire and to operate. The acquisition and use of OCDM and OCDE, among diverse particles, elements and energies, atomic and subatomic, may be accomplished by other proprietary methods as discovered within the scope of this invention.

Various embodiments and methods to acquire OCDM and OCDE are found here, and all are considered to be within the scope of this invention, including, but not limited to:
- spectroscopic methods
  - Raman,
  - SERS
  - CARS
  - Stokes
  - anti-stokes
  - scalar wave
  - Rayleigh microscopy
- the use of
  - photons
  - protons
  - electrons
  - neutrons
  - particle colliders
  - particle accelerators
  - signal beam splitting
  - particle duality states
  - manipulation of particles
  - temporal manipulations of particles or energies
  - laser sources
  - laser emissions
  - diode emissions
  - quantum tunneling
  - product of quantum tunneling
  - electron flows
  - electronic pulse
  - alternating current electricity
  - direct current electricity
  - plasma, plasma fields
- any form of radiation including
  - microwave
  - oscillation
  - optical generating
  - optical signal
  - optical pulses
  - semiconductor
  - superconductors
  - supercooled semiconductors
  - superposition particles
  - super symmetry
  - wave packages
  - wave energies
  - unknown energy waves
- energies of
  - harmonic frequencies
  - acoustic vibrations
  - vibrational energies
  - known and unknown atomic and sub atomic particles
  - supercooled atomic and subatomic particles
  - superheated atomic and subatomic particles
  - gravitational fields
  - gravitational energies
  - solar energies
  - magnetic energies
  - magnetic resonance
  - super magnets
  - unnamed particles and fields
  - elements
  - supercooled or superheated elements.

These embodiments and methods, and any product and application of these methods are considered to be within the scope of this discovery and invention.

Figure 1:
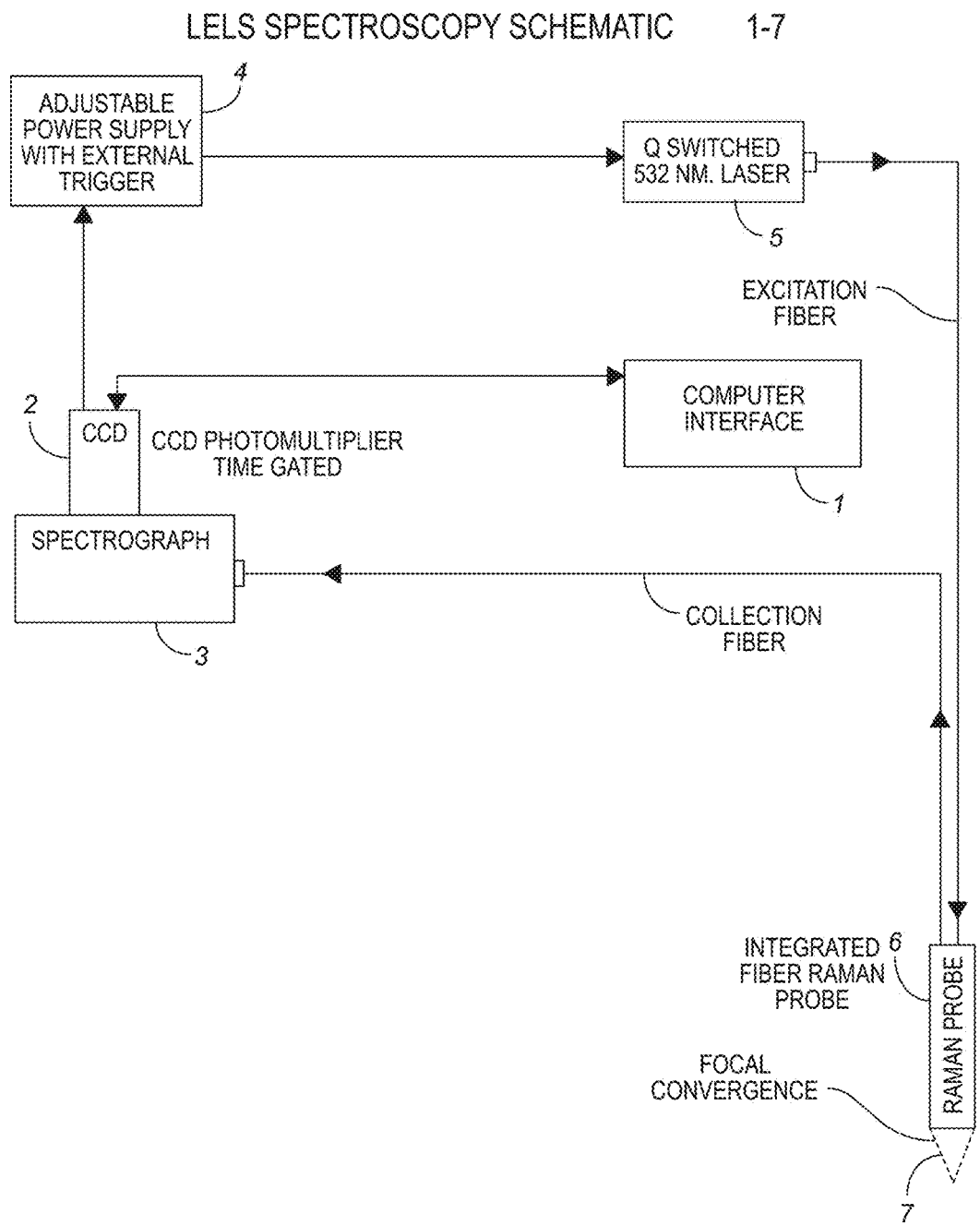

FIG. 1 is a block diagram of a low energy laser spectroscopy system constructed in accordance with the present subject matter. A computer interface 1 is coupled to the LELS platform system. A USB 2.0 cable couples the computer interface 1 to an ICCD camera and photomultiplier 2, or another scanner-detector, according to an illustrative embodiment of the invention. The ICCD camera and photomultiplier 2 is coupled to a spectrograph 3 and to an external trigger of an adjustable external power supply 4. The spectrograph 3 is coupled to the ICCD camera and photomultiplier 2. The adjustable external power supply 4 is coupled to a Q switched laser 5 by a cable from external trigger integrated into the ICCD camera and photomultiplier 2. The adjustable power supply 4 is coupled by cable to the laser 5.

The Q switched laser 5 is a green 532 nm YAG Laser, or another laser, with excitation fiber cable output to a Raman probe 6. The Raman probe 6 has two RF shielded internally connected coated fiber optic cables. A cable from the laser 5 couples excitation emissions to Raman probe 6. Collections of energies leaving the probe 6 are transmitted to and coupled to the spectrograph 3.

Emissions energies are transmitted from the laser 5 through the Raman probe 6 to a sample specimen for irradiation via a focal convergence field 7. The collections of the product of the irradiated sample return through the focal convergence field 7 into Raman probe 6 and thereon transmitted through collections fiber to spectrograph 3.

Figure 2A:
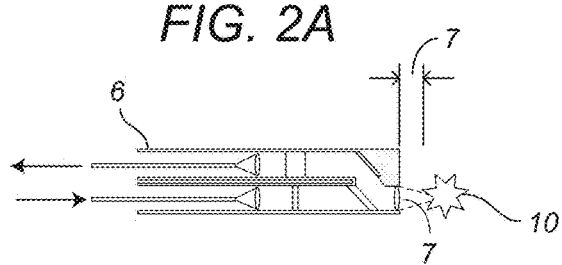
FIG. 2B is a cross-sectional illustration of a single fiber optic strand transmitting and receiving energy within the present system.
FIG. 2C is a cross-sectional illustration of a mechanical coupling for stabilizing the optical fiber of FIG. 2B.
FIG. 2D is a cross-sectional illustration of the mechanical coupling and fiber-optic strand mechanically coupled in axial alignment with the Raman probe of FIG. 2A.
FIG. 2E is a plot of spectral data received by the Raman probe of FIG. 2A from a first irradiated sample specimen.
FIG. 2F is a plot of spectral data received by the Raman probe of FIG. 2D from the first irradiated sample specimen.
FIG. 2G is a printout of a nominal LELS system run and spectroscopic analysis.

FIG. 2 consists of FIGS. 2A through 2G, wherein FIG. 2A is a cross-sectional illustration of the Raman probe 6 which both excites and collects energy from a specimen sample 10. A fiber optically coupled Raman probe 6 comprises one or more strands. Fiber optic coating and RF shielding connects the laser 5 energy transmission to and through optics of the Raman probe 6 through a focal lens producing a convergence field 7 having a length of 5 mm for both excitation and collections of energies from specimen sample 10. The focal lens redirects the energies from the excited specimen 10 to a diachronic mirror and a secondary mirror through a second fiber optic strand or strands through the Raman probe 6 which transmits irradiated sample energies back to the spectrograph 3.

Figure 2B:
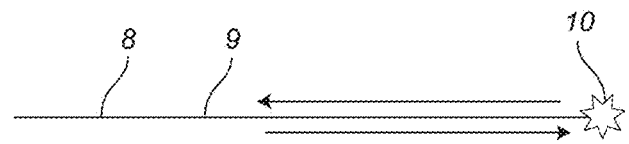

FIG. 2B is a cross-sectional illustration of a single fiber optic strand transmitting and receiving energy within the present system. A flexible single fiber optic strand 8 is provided. A long length single strand fiber optic (LLFO) 9 is coated and shielded from ambient light and may exceed 18" in length. The LLFO 9 comprises the fiber optic strand 8.

Figure 2C:
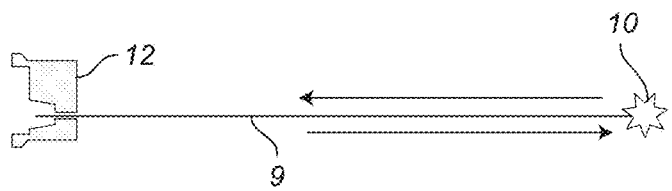

FIG. 2C is a cross-sectional illustration of a mechanical coupling 12 for stabilizing the LLFO 9. The LLFO 9 is inserted 2 mm into and through a coupling 12 to stabilize the LLFO into the standard 5 mm convergence field 7 of the Raman probe 6.

Figure 2D:
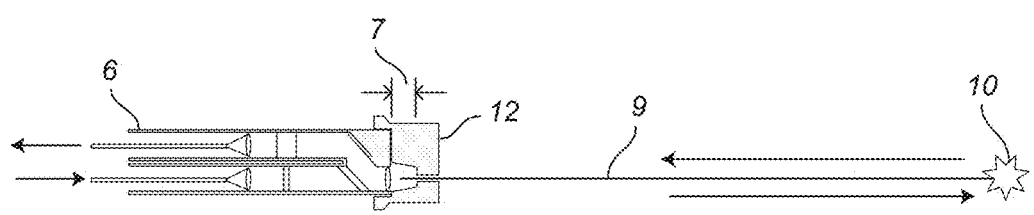

FIG. 2D is a cross-sectional illustration of the mechanical coupling of LLFO 9 in axial alignment with the Raman probe 6. The length of the convergence field 7 is extended by coupling the LLFO 9 2 mm into the convergence field 7, thereby gaining a longer laser convergence field 7. The longer convergence field 7 irradiates and excites specimen sample 10 and collects and returns emissions data through the same strand of LLFO 9 simultaneously.

Figure 2E:
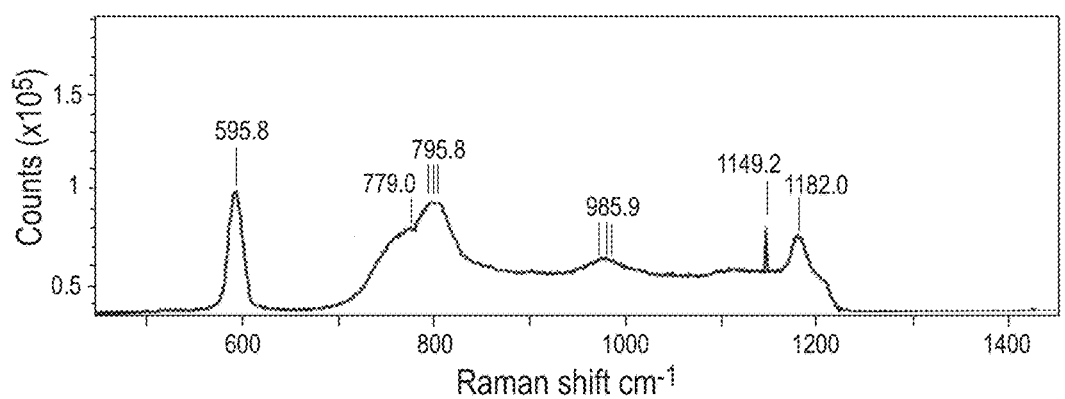
Figure 2F:
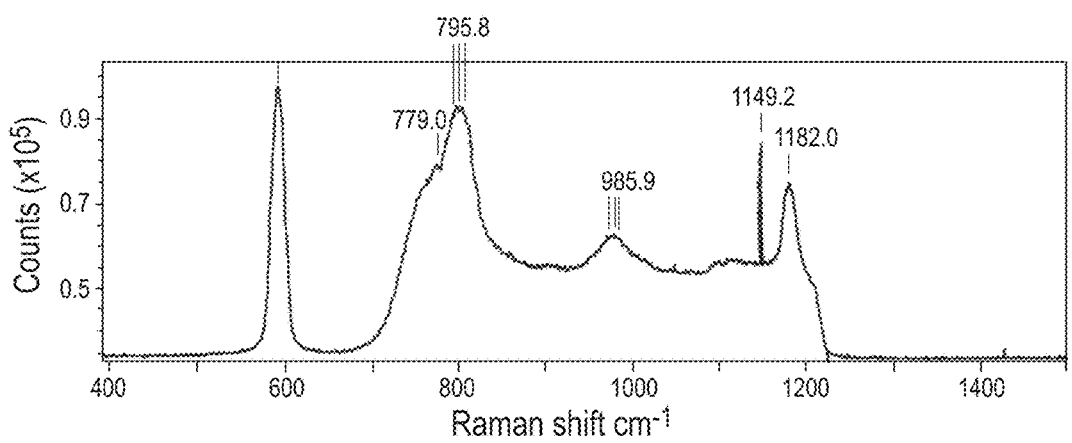

FIGS. 2E and 2F are each a plot of spectral data received by the Raman probe 6 from an irradiated sample specimen 10 of carbon fluorine perflourdecalin C10 F18. Perflourdecalin C10 F18 is one of several formulations of synthetic blood.

In FIG. 2E spectral data is obtained using a Raman probe according to FIG. 2A. Spectral data of FIG. 2F is received through the LLFO 9 by the Raman probe of FIG. 2D. Extending the length of the convergence field 9 by inserting an LLFO 9 into the standard laser convergence field gained at least a 600% longer laser convergence field 7 working range. The spectral image in FIG. 2F shows increased sensitivity and higher peaks compared to data of the same specimen as seen in FIG. 2 E.

FIG. 2G is a printout of a nominal LELS system run and spectroscopic analysis producing spectra of the type seen in FIG. 2E and FIG. 2F. A photon count in the penultimate line of FIG. 2G reads "false." On computer spectral runs, most of the photons will scatter on the surface or absorb into packaging material through sampling process. The OCDM and OCDE among unknown energies or particles complete tunneling into material, irradiating the material, collecting data, returning energies through same open tunnel to the spectrograph 3 and recording of data.

FIG. 3 consists of FIGS. 3A through 3E, wherein FIG. 3A is a cross-sectional view of an LLFO 9 comprising a single fiber-optic strand 8. The flexible single fiber optic strand 8 may exceed 18" in length. The long length single strand fiber optic LLFO 9 is coated and shielded from ambient light.

FIG. 3B is a cross-sectional illustration of the single fiber optic strand of FIG. 3A inserted into a medical syringe 13. One length out of variable lengths of the LLFO 9 is inserted 2 mm through a neoprene alignment stop located in the syringe 13 where an axial end of the Raman probe 6 will rest. FIG. 3C is a cross-sectional illustration of a biopsy needle 14 having the LLFO 9 pre-inserted and being affixed to the syringe 13.

FIG. 3D is a cross-sectional illustration in which the Raman probe 6 is located in the syringe 13 to comprise a bioprobe. A one-time use sterile covering is used over bioprobe for medical usage. The single strand LLFO 9 within a sterile biopsy probe, syringe 13 and needle 14, with standard Raman biopsy probe 6 inserted into a plastic syringe, 13-14 placed within 4 to 5 mm. of sample in-vivo tissue specimen without intrusion into specimen or tumor. The energies carried through LLFO 9 irradiate specimen 10 and collect irradiated specimen energies back through the same single strand LLFO 9 in same time.

FIG. 3E is a plot of spectral data obtained by the bioprobe according to FIG. 3D from irradiated sample specimen 10 of carbon fluorine perflourdecalin chemical composition, which is a C10F18 biomarker through LLFO 9 and syringe 13 coupled to needle 14 and method of extending the length of the standard convergence 7 by inserting a long length fiber optic strand 9 into the standard laser convergence field 7 therefore gaining a 600+% longer laser convergence field working range. Again, extending the length of the standard convergence field 7 by inserting an LLFO 9 into the convergence field 7 provides at least a 600% longer laser convergence field 7 working range. FIG. 3E shows increased sensitivity and higher peaks through the LLFO 9 acquired specimen energies and data through the long length bio probe compared to data of the same specimen acquired through Raman probe 6 and convergence length 7 as seen in the spectrum of FIG. 2E.

FIG. 4 consists of FIGS. 4A and 4B, wherein FIG. 4A is a diagram of one form of quantum well laser diode suitable for use in the present Raman probe.

FIG. 4A illustrates a laser quantum well 15 region of quantum tunneling and weak diode effect, where secondary quantum tunneling and secondary wave package and entanglement occurs. The present subject matter is not limited to a specific configuration.

FIG. 4B illustrates a further form of laser diode comprising a separate confinement laser quantum well 15. The laser quantum well 15 also comprises a region of quantum tunneling and weak diode effect in quantum well, where secondary quantum tunneling and secondary wave package and entanglement occurs.

In FIG. 5, consisting of FIGS. 5A and 5B, FIG. 5A comprises a spectrum plot 16 of Bayer® aspirin, C9H8O4, as radiated through a blister pack container, Spectrum 17 is produced by the same tablet irradiated outside of blister pack with photons still in entanglement. The spectrum 16 has a higher energy count than in spectrum 17. Photons scatter on and lose energy through absorption on solid surfaces. The remaining energies tunneling through the blister pack and into the solid tablet are particles and OCDM and OCDE. After irradiating the solid pharmaceutical tablet specimen, the unknown particles and OCDM and OCDE return irradiated specimen energies back through the open tunnel of the blister pack and back through the LELS system on to analysis and spectral display. This increase in energy count through a solid object is atypical of all other Raman spectroscopy.

FIG. 5B comprises a spectrum 18 of Zyrtec® cetirizine irradiated through a blister pack. Spectrum 19 is for Zyrtec Cetirizine® irradiated outside of the blister pack. The spectrum 18 has a higher energy count. This increase in energy count through a solid object is atypical of all other Raman spectroscopy. In FIG. 5B, spectrum 19 for Zyrtec pharmaceutical tablet irradiated outside of blister pack has a lower energy count.

Figure 6A:
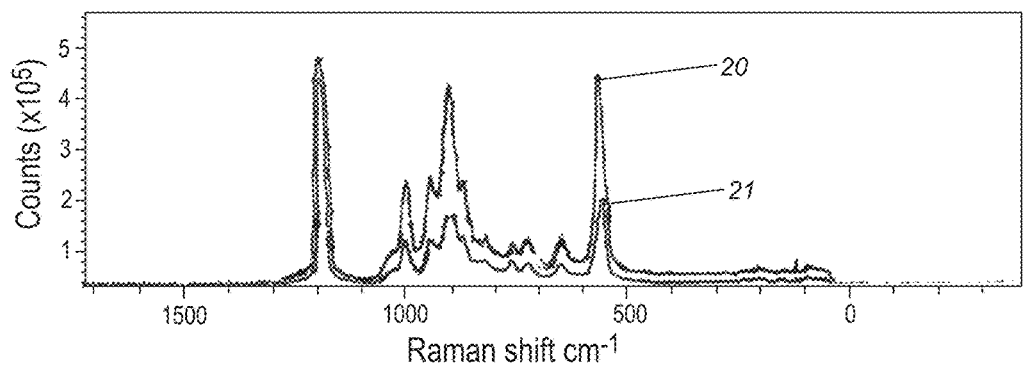
Figure 6B:
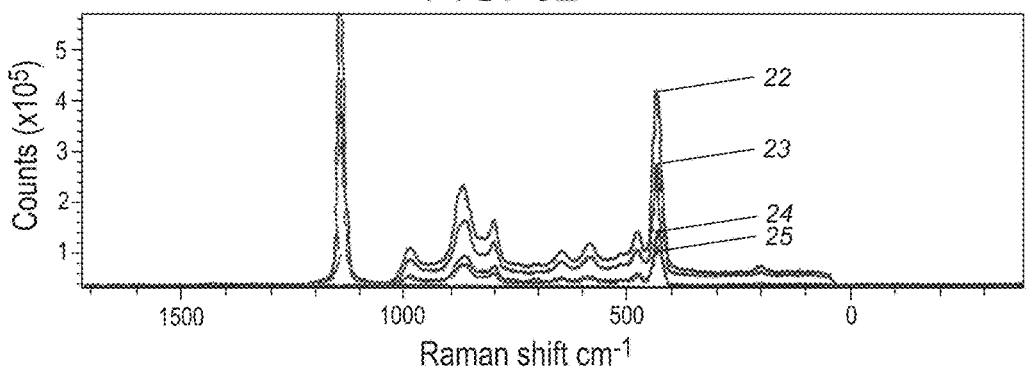
Figure 6C:
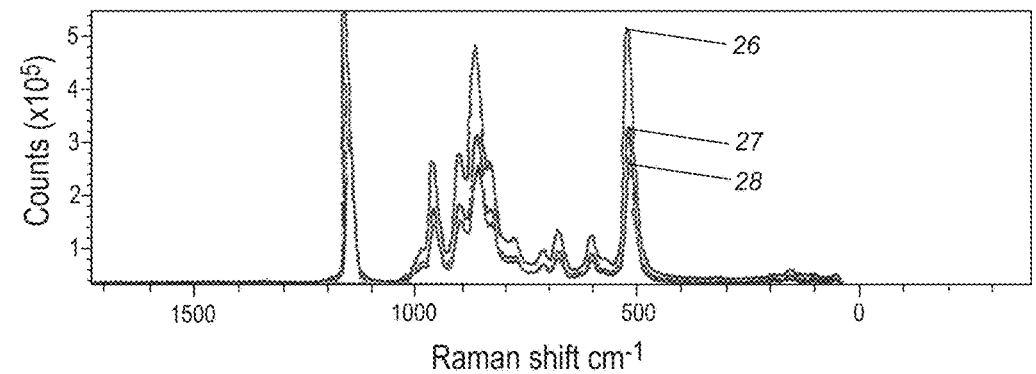

FIG. 6 consists of FIGS. 6A through 6E, each of which represents a spectrum for a different composition. In FIGS. 6A, 6B and 6C, the spectral count in spectra 20 through 28 increases incrementally on subsequent readings of the sample 10.

In FIG. 6A a spectrum 21 is generated from a static sample 10 of a carbon fluorine bond perflourdecalin chemical composition. The sample 10 is not vibrated or stirred prior to irradiating and collecting spectral data as shown. In order to generate the spectrum 20 the sample 10 perflourdecalin C10F18 is mixed, stirred, agitated in a test tube. Thirty seconds after agitating, the sample 10 is irradiated and the data is collected. The spectral results after sampling and collecting specimen data show an approximately 300% increase in energy count compared to the spectrum 21 of a static sample.

FIG. 6B illustrates actual spectra of sample 10 of carbon fluorine bond hexane chemical composition C6F14. The sample is irradiated and energies collected through LELS method. Spectra 25-22 are produced from a sample in the same test tube as follows:

25—static
24—vibrated, sampled after 30 seconds
23—vibrated, sampled after 5 minutes
22—vibrated, sampled after 20 minutes.

A notable energy count increase occurs after each successive time period.

FIG. 6C represents spectra of a carbon fluorine bond perflourdecalin C10F18.

Spectra 28-26 are produced from a sample in the same test tube as follows;
28—static
27—vibrated, sampled after 30 seconds
26—vibrated, sampled after 5 minutes.

With respect to spectra 21 through 28, the spectral count on the imaging device, the CCD photomultiplier 2 (FIG. 1), increases incrementally on subsequent readings of the spectra sample many minutes after initial excitation, evidencing continued propagation of energy and a time differential, a temporal delay. Evolving in free space, the time-dependent momentum and position space wave functions are:

$$\Phi(p, t) = \left(\frac{x_0}{\hbar\sqrt{\pi}}\right)^{1/2} \cdot \exp\left(\frac{-x_0^2(p-p_0)^2}{2\hbar^2} - \frac{ip^3 t}{2m\hbar}\right),$$

$$\Psi(x, t) = \left(\frac{1}{x_0\sqrt{\pi}}\right)^{1/2} \cdot \frac{e^{-x_0^2 p_0^2/2\hbar^2}}{\sqrt{1+i\omega_0 t}} \cdot \exp\left(\frac{(x^{-i}x_o^2 p_0/\hbar)^2}{2x_0^2(1+i\omega_0 t)}\right)$$

Since $\sigma_p(t) = \hbar/x_0\sqrt{2}$, this can be interpreted as a particle moving along with constant momentum at arbitrarily high precision.

On the other hand, the standard deviation of the position is $$\sigma_x = \frac{x_0}{\sqrt{2}}\sqrt{1+\omega_0^2 t^2}$$

such that the uncertainty product can only increase with time as:

$$\sigma_x(t)\sigma_p(t) = \frac{\hbar}{2}\sqrt{1+\omega_0^2 t^2}.$$

Figure 6D:
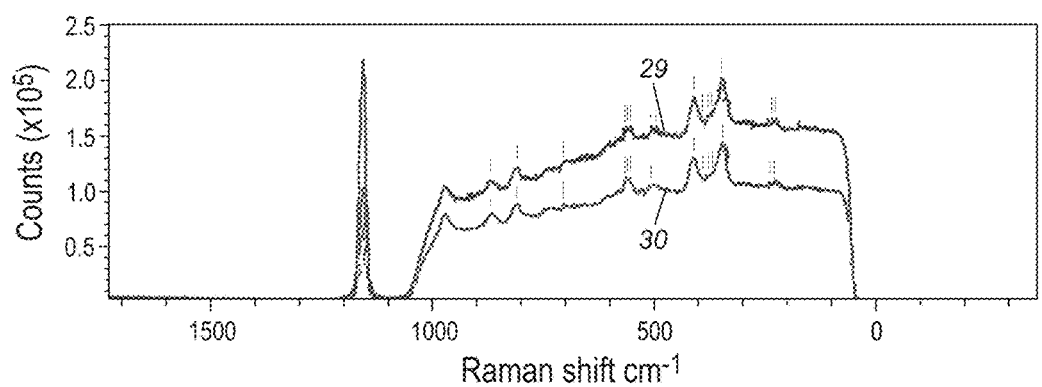

FIG. 6D represents actual spectra of energies collected from a sample of Tylenol® acetaminophen, C8H9N02. Spectrum 30 is obtained from a static sample. The spectrum 29 is produced from a vibrated sample and shows a notable increase in energies and spectral information.

Figure 6E:
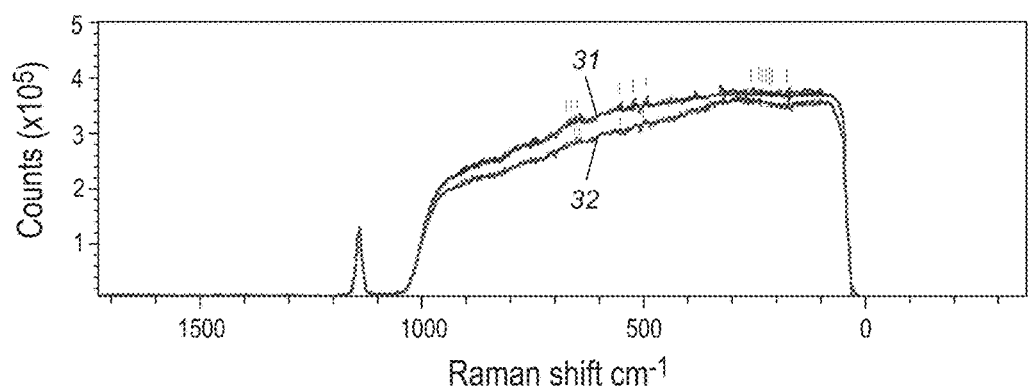

FIG. 6E represents spectra 32 and 31 of Lipitor® atorvastatin, C33H35FN2O5 for static and vibrated samples respectively.

FIG. 7 consists of FIGS. 7A through 7E which represent spectra of different pharmaceuticals.

FIG. 7A illustrates spectra for three different forms of aspirin tablets. The tablets are irradiated separately by the same LELS method with no prior tablet preparation. Each sample is processed identically, irradiated, and the energies collected through the Raman probe 6 and sent on to computer analysis and spectral display.

The spectra correspond to each form of aspirin as follows:
33—Bayer® aspirin
34—counterfeit aspirin tablet brand #1
35—counterfeit aspirin tablet brand #2

A spectral comparison between the brand name aspirin tablet and two separate brands of generic or counterfeit aspirin tablets is provided. Spectrum 34 for generic tablet #1 differs markedly from brand name tablet spectrum 33 and slightly differs from generic tablet spectrum 35 for generic tablet #2. Spectrum 35 for counterfeit tablet #2 differs markedly from brand name tablet spectrum 33 and differs slightly from spectrum 34 produced from counterfeit tablet #2.

This demonstration of the sensitivity of the LELS method of detecting minute differences in percentage of chemicals in similar compounds may be used for many chemical compound analyses with real time results.

FIG. 7B illustrates comparison of a spectrum 36 generated from Lipitor® atorvastatin tablet and a spectrum 37 generated from a generic atorvastatin tablet. Both the solid brand name tablet and the solid counterfeit tablet are factory coated.

Each tablet was irradiated separately, by the same LELS method with no prior tablet preparation. Each sample is irradiated, and the energies collected through LELS method sent on to computer analysis and spectral display.

Spectrum 36 corresponding to Lipitor® atorvastatin brand has a higher percentage of the chemical compound of the pharmaceutical chemical signature C35H35FN2O5. Spectrum 37 corresponding to generic atorvastatin shows a lower percentage of the active ingredient C35H35FN2O5.

FIG. 7C represents a real time rapid assay and spectral results of pharmaceutical identification of Tylenol® acetaminophen, C8H9NO2. The spectrum of FIG. 7C is made with no prior preparation of Tylenol, with noiseless spectral results.

FIG. 7D represents a spectrum generated from Cipro® ciprofloxacin hydrochloride, C17H18FN3O3*HCI*H2O. The spectrum is generated from a solid tablet of Cipro ciprofloxacin hydrochloride made with no prior preparation, providing a clear spectrum.

FIG. 7E represents a spectrum generated from a solid tablet of Motrin® ibuprofen, C13H18O2, made with no prior preparation.

FIG. 8 consists of FIGS. 8A through 8F, each representing the spectrum of a respective mineral or gemstone. Each sample is measured without prior preparation. The present LELS method of spectroscopy accomplishes same-time geological, metallurgical, gemology, assay and verification. The low energy device has reliably unique properties, extreme sensitivity, diversity and functionality.

Figure 8A:
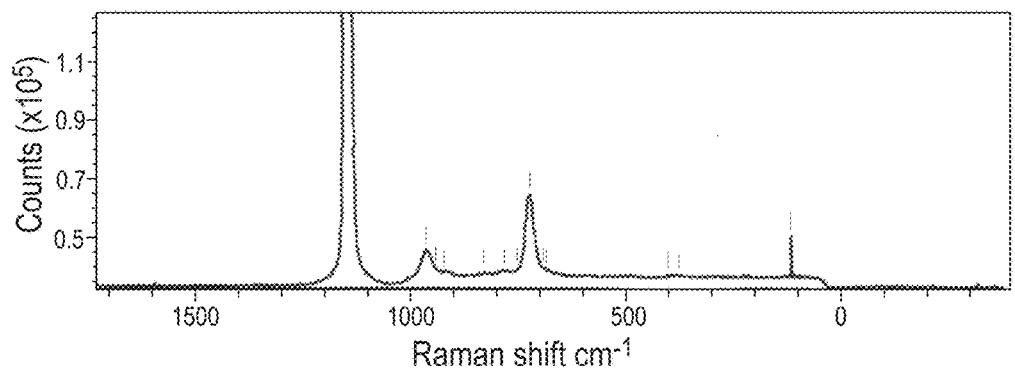

FIG. 8A represents a spectrum generated from amethyst crystal natural dark purple coloring. Amethyst comprises SiO2 with minor Fe4+ impurities causing amethyst's color. The amethyst is of the class tectosilicate and has a hexagonal-R, 32(trigonal-trapezohedral) crystal system.

Figure 8B:
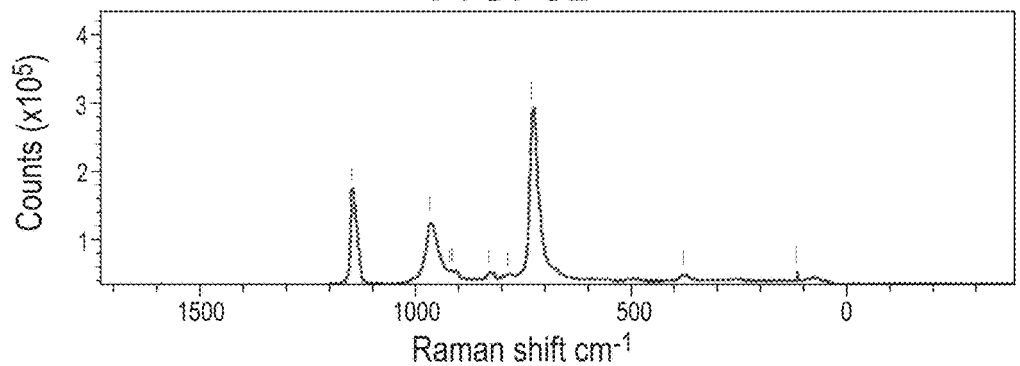

FIG. 8B represents a spectrum generated from quartz, a form of SiO2 of the class tectosilicate and having a hexagonal-R, 32(trigonal-trapezohedral) crystal system.

Figure 8C:
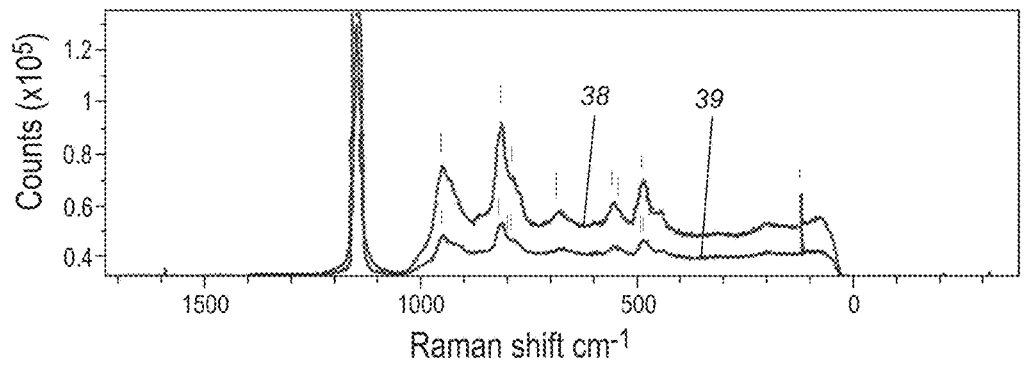

FIG. 8C represents spectra generated from tourmaline crystal. Elbaite is the most well-known individual member mineral of the tourmaline group. Elbaite is the most transparent and colorful form of tourmaline. The term elbaite may be corrupted in the gemstone industry to refer specifically to green tourmaline.

Spectrum 38 is generated from green elbaite, (Na,Ca)(Mg,Li,Al,Fe2+) 3Al6(BO3)3Si6O18(OH)4.

Spectrum 39 is generated from rubellite, a pink to red variety of elbaite tourmaline.

Figure 8D:
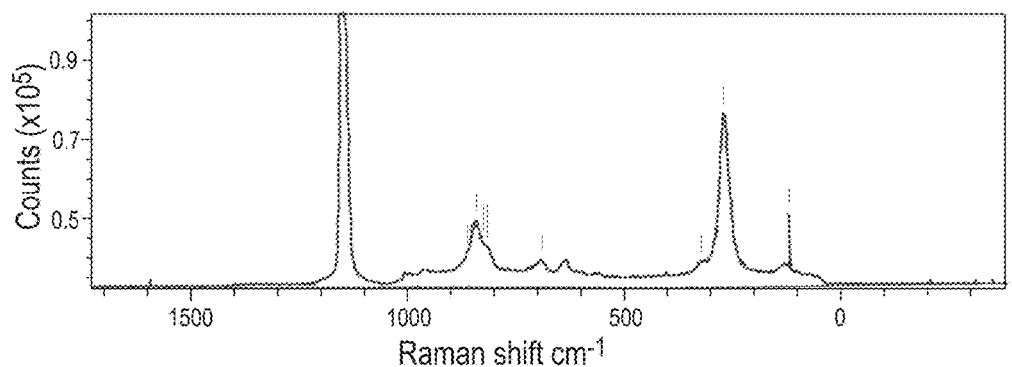

FIG. 8D represents a spectrum generated from an almandine garnet crystal, Fe3Al2(SiO4)3.

Figure 8E:
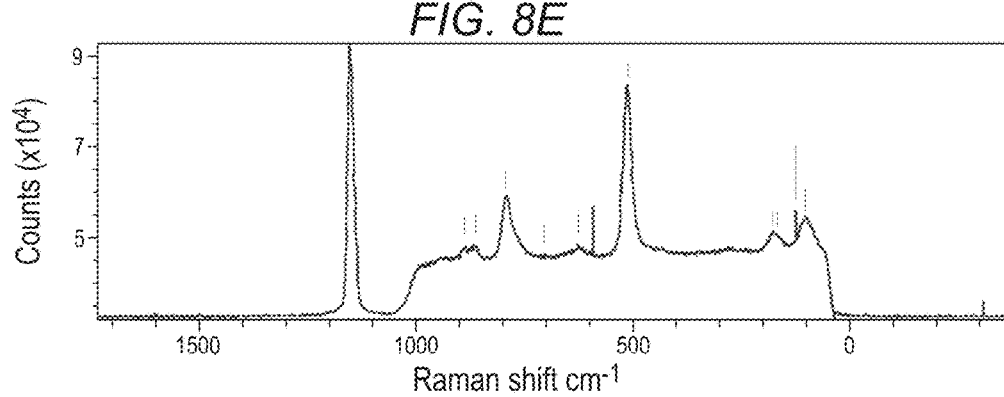

FIG. 8E represents a spectrum generated from clear morganite crystal, Be3Al2(SiO3)6.

Figure 8F:
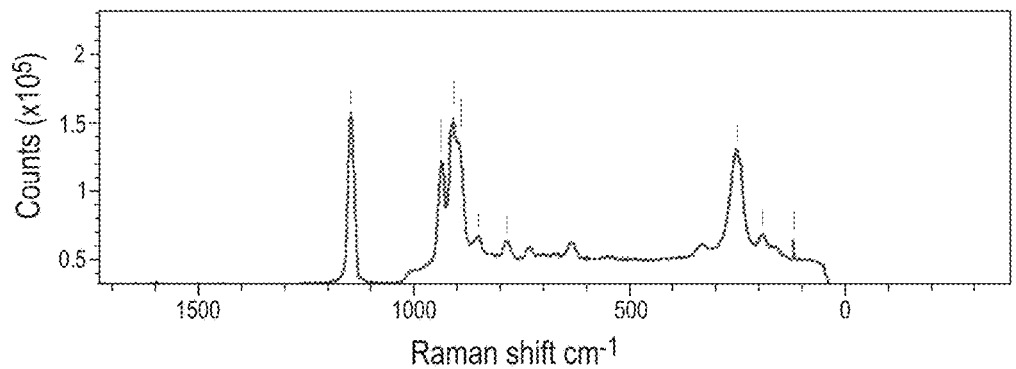

FIG. 8F represents a spectrum generated from clear crystal topaz, (Al2SiO4(F,OH)2).

Figure 9A:
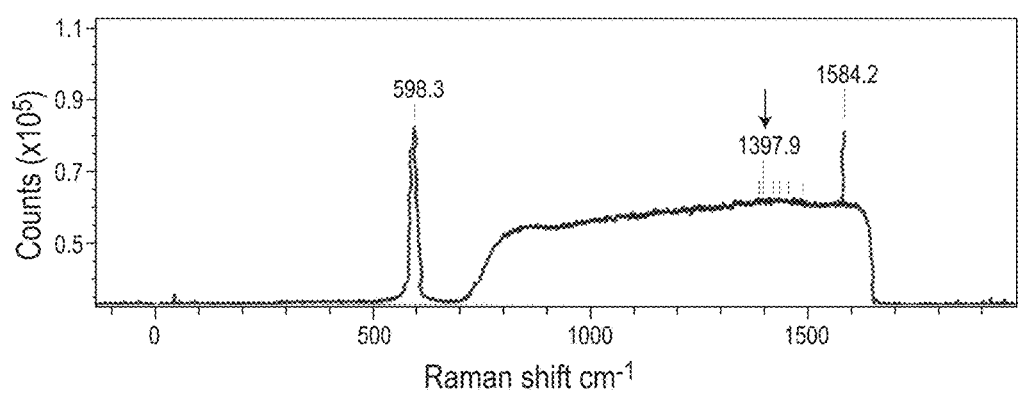

FIG. 9 consists of FIGS. 9A through 9D, each representing a spectrum of a sample containing a noble metal. Samples respectively associated with each figure are as follows:

FIG. 9A—0.925 sterling silver (Ag with a shiny surface)

Figure 9B:
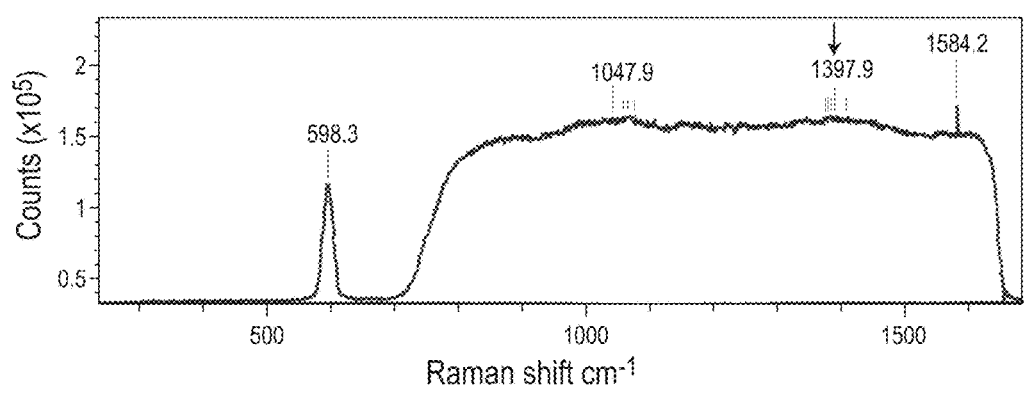
Figure 9C:
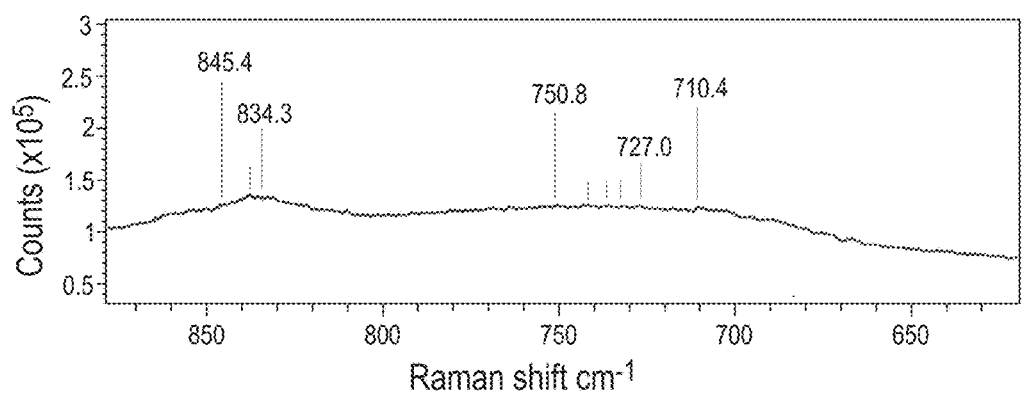

FIG. 9B—silver sulfate ointment (Ag 1% silver in solution)

FIG. 9C—14 karat gold (58.65% gold AU at 710.4 nm on the spectrum)

Figure 9D:
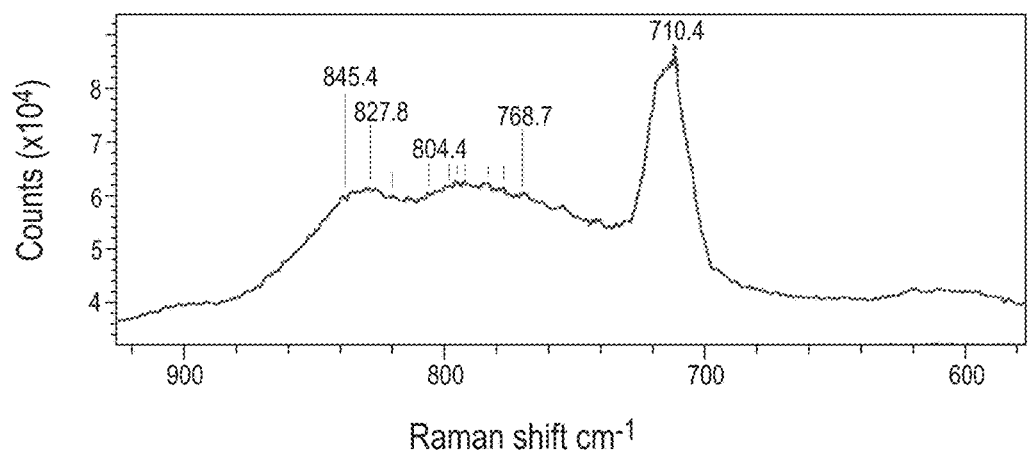

FIG. 9D—a typical rough ore sample from tourmaline mine.

The particular rough ore sample of FIG. 9D exhibits traces of silicates and gold at 710.4 nm on the LELS spectrum.

Further details of each of the concepts utilized in the method and apparatus described above may be understood by reference to the following publications.

Quantum Mechanics

1. Einstein A, Podolsky B, Rosen N (1935. "Can Quantum-Mechanical Description of Physical Reality Be Considered Complete?". Phys. Rev. 47 (10): 777-780. Bibcode: 1935PhRv . . . 47 . . . 777E. doi:10.1103/PhysRev.47.777.
2. Schrodinger E; Born, M. (1935. "Discussion of probability relations between separated systems". Mathematical Proceedings of the Cambridge Philosophical Society 31 (4): 555-563. doi:10.1017 IS03050041000135554.
3. Schrodinger E; Dirac, P. A. M. (1936. "Probability relations between separated systems". Mathematical Proceedings of the Cambridge Philosophical Society
4. Alisa Bokulich, Gregg Jaeger, Philosophy of Quantum Information and Entanglement, Cambridge University Press, 2010, xv.
5. 1. Olaf Nairz. Markus Arndt. and Anton Zeilinger. "Quantum interference experiments with large molecules", American Journal of Physics, 71 (April 2003 319-325.
6. "Wave functions could describe combinations of different states, so-called superpositions. For example, an electron could be in a superposition of several different locations", from Max Tegmark; John Archibald Wheeler (2001. "100 Years of the Quantum". Sci. Am.: Spektrum Wiss. Dossier N1:6-14 284 (2003): 68-75. arXiv:quant-ph/0101077.
7. Brian Greene, The Fabric of the Cosmos, p. 11 speaks of "an instantaneous bond between what happens at widely separated locations."
8. Fischer, A M; et al. (2009. "Exciton Storage in a Nanoscale Aharonov-Bohm Ring with Electric Field Tuning". Physical Review Letters 102: 096405. arXiv: 0809.3863. Bibcode:2009PhRvL.102i6405F. doi: 10.1103/PhysRevLett.102.096405.
9. M. Tsubota, K. Inagaki, T. Matsuura and S. Tanda (2012. "Aharonov-Bohm effect in charge-density wave loops with inherent temporal current switching". EPL (Europhysics Letters 97 (5): 57011. arXiv:0906.5206. Bibcode: 2012E L . . . 9757011T. doi:10.1209/0295-075/97/57011.
10. Chernyak, V Y; Sinitsyn, N A (2009. "Robust quantization of a molecular motor motion in a stochastic environment". Journal of Chemical Physics 131 (18): 181101. arXiv:0906.3032. Bibcode:2009JChPh.131r1101C. doi: 10.1063/1.3263821. PMID 19916586.
11. "Decoherence was worked out in great detail by Los Alamos scientist Wojciech Zurek, Zeh and others over the following decades. They found that coherent quantum superpositions persist only as long as they remain secret from the rest of the world." from Max Tegmark; John Archibald Wheeler (2001. "100 Years of the Quantum". Scientific American 284(2003): 68-75. arXiv:quant-ph/O101077.:10.1038/scientificamerican0201-68.
12. Matson, John. Quantum teleportation achieved over record distances. Nature, 13 Aug. 2012
13. Francis, Matthew. Quantum entanglement shows that reality can't be local, Ars Technica, 30 Oct. 2012
14. Einstein A, Podolsky B, Rosen N (1935. "Can Quantum-Mechanical Description of 15. Physical Reality Be Considered Complete?". Phys. Rev. 47 (10): 777-780. 16. Bibcode:1935PhRv . . . 47 . . . 777E. doi:10.1103/PhysRev.47.777.
17. 15. Schrodinger E; Born, M. (1935. "Discussion of probability relations between separated systems". Mathematical Proceedings of the Cambridge Philosophical Society (4): 555-563. doi:10.1017 IS03050041000135554.
18. 16. Schrodinger E; Dirac, P. A. M. (1936. "Probability relations between separated systems". Mathematical Proceedings of the Cambridge Philosophical Society (3): 446-452. doi:10.1017/S03050041000191137.
19. Letter from Einstein to Max Born, 3 Mar. 1947; The Born-Einstein Letters; Correspondence between Albert Einstein and Max and Hedwig Born from 1916 to 1955, Walker, N.Y., 1971. Cited in M. P. Hobson; et al. "Quantum Entanglement and Communication Complexity (1998)". pp. 1/13. CiteSeerX: 10.1.1.20.8324. J. S. Bell (1964. in the Einstein-Poldolsky-Rosen paradox". Physics
20. Freedman, Stuart J.; Clauser, John F. (1972. "Experimental Test of Local Hidden-Variable Theories". Physical Review Letters 28 938-941.Bibcode:1972PhRvL . . . 28 . . . 938F. doi:10.1103/PhysRevLett. 28.938.
21. Freedman, Stuart J.; Clauser, John F. (1972. "Experimental Test of Local Hidden-Variable Theories". Physical Review Letters 28 938-941.Bibcode:1972PhRvL . . . 28 . . . 938F. doi:10.1103/PhysRevLett. 28.938.
22. Freedman, Stuart J.; Clauser, John F. (1972. "Experimental Test of Local Hidden-Variable Theories". Physical Review Letters 28 938-941.Bibcode:1972PhRvL . . . 28 . . . 938F. doi:10.1103/PhysRevLett.28.938.
23. 20. Aspect, P. Grangier, and G. Roger (1982. "Experimental Realization of Einstein-Podolsky-Rosen-Bohm Gedanken experiment: A New Violation of Bell's Inequalities". Physical Review Letters (2): 91-94. Bibcode:1982PhRvL . . . 49 . . . 91A. doi:10.1103/PhysRevLett.49.91.
24. Asher Peres, Quantum Theory, Concepts and Methods, Kluwer, 1993; ISBN 0-7923-2549-p. 115.
25. Cirel'son, B. S. (1980. "Quantum generalizations of Bell's inequality". Letters in Mathematical Physics 4 (2): 93-100. Bibcode:1980LMaPh . . . 4 . . . 93C. doi:10.1007/BF00417500.
26. H. Zbinden, et al. (2001. "Experimental test of nonlocal quantum correlations in relativistic configurations". Phys. Rev. A. doi:10.1103/PhysRevA.63.022111.
27. Zbinden, et al. experiments is provided in Gilder, L., The Age of Entanglement, Vintage Books, 2008, pp. 321-324.
28. Xiao-song Ma, Stefan Zotter, Johannes Kofler, Rupert Ursin, Thomas Jennewein, Caslav Brukner & Anton Zeilinger (26 Apr. 2012. "Experimental delayed-choice entanglement swapping". Nature Physics. doi:10.1038/nphys2294.
29. E. Megidish, A Halevy, T. Shacham, T. Dvir, L. Dovrat, and H. S. Eisenberg, "Entanglement Swapping between Photons that have Never Coexisted", Physical Review Letters, Volume 110, Issue 21, 22 May 2013.

30. (http://plato.stanford.edu/entries/qt-eprl) Niels Bohr distinguished between "mechanical disturbances" and "an influence on the very conditions which define the possible types of predictions regarding the future behavior of the other half of an entangled] system."
31. Sidney Coleman: Quantum Mechanics in Your Face—Sidney Coleman New England sectional meeting of the American Physical Society (Apr. 9, 1994 http://media.physics.harvard.edu/video 1?id=SidneyColemanQMIYF
32. Locality in the Everett Interpretation of Heisenberg-Picture Quantum Mechanics http://arxiv.org/abs/guant-ph/0103079
33. Werner, R. F. (1989. "Quantum States with Einstein-Podolsky-Rosen correlations admitting a hidden-variable model". Physical Review A (8): 4277-4281.doi:10.1103/PhysRevA40.4277. PMID 9902666.
34. Jaeger G, Shimony A, Vaidman L (1995. "Two Interferometric Complementarities". Phys. Rev. (1): 54-67. Bibcode:1995PhRvA.51 . . . 54I. doi:10.1103/PhysRevA51.54.
35. Nielsen, Michael A; Chuang, Isaac L. (2000. Quantum Computation and Quantum Information. Cambridge University Press. pp. 112-113. ISBN 0-521-63503-9.
36. Laloe, Franck (2012), Do We Really Understand Quantum Mechanics, Cambridge University Press, ISBN 978-1-107-02501-1
37. Gurvits L (2003. "Classical deterministic complexity of Edmonds' Problem and quantum entanglement". Proceedings of the thirty-fifth annual ACM symposium on Theory of computing: 10. doi:10.1145/780542.780545. ISBN 1-58113-674-9.
38. Horodecki M, Horodecki P, Horodecki R (1996. "Separability of mixed states: necessary and sufficient conditions". Physics Letters A 223: 210. arXiv:quant-ph/9605038.Bibcode:1996PhLA . . . 223 . . . 1H. doi: 10.1016/S0375-9601(96)00706-2.
39. Dirac, P. A. M. (2008. "Note on Exchange Phenomena in the Thomas Atom". Mathematical Proceedings of the Cambridge Philosophical Society 26 (3): 376. Bibcode: 1930PCPS . . . 26 . . . 376D. oi:10.1017/S0305004100016108.
40. Fan, H; Korepin V, Roychowdhury V (2004-11-26. "Entanglement in a Valence-Bond Solid State". Physical Review Letters 93 (22): 227203. arXiv:quant-ph/0406067.Bibcode:2004PhRvL . . . 93v7203F. doi: 10.1103/PhysRevLett.93.227203. PMID 15601113.
41. Franchini, F.; Its, A. R.; Korepin, V. E.; Takhtajan, L. A. (2010. "Spectrum of the density matrix of a large block of spins of the X Y model in one dimension". Quantum Information Processing(3): 325-341. arXiv:1002.2931. doi:10.1007/s11128-010-0197-7.
42. Cerf, Nicolas J.; Cleve, Richard. "Information-theoretic interpretation of quantum error-correcting codes".
43. Plenio; Virmani (2007. "An introduction to entanglement measures". Quant. In! Comp. 1: 1-51. arXiv:quant-ph/0504163. Bibcode:2005quant.ph . . . 4163P.
44. Bouwmeester, Dik; Pan, Jian-Wei; Mattle, Klaus; Eibl, Manfred; Weinfurter, Harald & Zeilinger, Anton (1997. "Experimental Quantum Teleportation" (PDF. Nature 390: 575-579.
43. Richard [ozsa: Noah Linden (2002. "On the role of entanglement in quantum computational speed-up". Proceedings of the Royal Society A: Mathematical, Physical and Engineering Sciences 459 (2036): 2011-2032. arXiv: quant-ph/0201143. bibcode:2003RSPSA.459.2011I. dOi: 10.1098/rspa.2002.1097.
44. Ekert, Artur K (1991. "Quantum cryptography based on Bell's theorem". Physical Review Letters (6): 661-663. doi:10.1103/PhysRevLett.67.661.PMID 10044956.
45. Karol Horodecki; Michal Horodecki; Pawel Horodecki; Ryszard Horodecki; Marcin Pawlowski; Mohamed Bourennane (2010. "Contextuality offers device-independent security". arXiv:1006.0468 [quant-ph].
46. Masahiro Kitagawa and Masahito Ueda, "Squeezed Spin States", Phys. Rev. A 47,5138-5143 (1993.
47. Phys. Rev. Lett. 71, 1355 (1993): Interferometric detection of optical phase shifts at the Heisenberg limit
48. Horodecki R, Horodecki P, Horodecki M, Horodecki K (2007. "Quantum entanglement". Rev. Mod. Phys. (2): 865-942. arXiv:quant-ph/0702225. Bibcode:2009RvMP . . . 81 . . . 865H.doi:10.1103/RevModPhys. Spectroscopy
1. M. J. Pelletier, Analytical Applications of Raman Spectroscopy Blackwell Science, Oxford, United Kingdom, 1999.
2. P. Matousek and A W. Parker, Appl. Spectrosc. 1353 (2006.
3. N. A Macleod and P. Matousek, Appl. Spectrosc. 291A (2008.
4. Emerging Raman Applications and Techniques in Biomedical and Pharmaceutical Fields, P. Matousek and M. D. Morris, Eds. (Springer, Heidelberg, 2010.
5. Matousek, I. P. Clark, E. R. C. Draper, M. D. Morris, A E. Goodship, N. Everall, M.
6. Towrie, W. F. Finney, and A W. Parker, Appl. Spectrosc. 393 (2005.
7. Eliassen, N. A. Macleod, and P. Matousek, Anal. Chem. 79,8185 (2007.
8. S. J. Johansson, S. Pettersson, and S. Folestad]. Pharmaceut. Biomed. 39,510 (2005.
9. P. Matousek and A. W. Parker]. Raman Spectrosc. 38,563 (2007.
10. P. Matousek and N. Stone, Analyst, 1058 (2009.
11. C. Eliasson and P. Matousek, Anal. Chem. 1696 (2007.
12. D. E. Pivonka, J. M. Chalmers, and P. R. Griffiths, Applications of Vibrational Spectroscopy in Pharmaceutical Research and Development (John Wiley & Sons, Chichester, 2007.
13. R. Salzer and H. W. Siesler, Infrared and Raman Spectroscopic Imaging (Wiley-VCH, Weinheim, 2009. 2006ApSpe . . . 60.1341M.oi:10.1366/000370206778999102. PIMID 17132454.
14. Hecht, Jeff. "Optics: Light for a New Age." Charles Scribner's Sons. 1987.
15. Hering, Peter, J. P. Lay and Sandra Story. "Laser in Environmental and Life Sciences" Springer. 2004.
16. Brancaleon L, Durkin A J, Tu J H, Menaker G, Fallon J D, Kollias N: In vivo fluorescence spectroscopy of non-melanoma skin cancer. Photochem Phobiol 2001,
17. R. Trebino, Frequency-Resolved Optical Gating: The Measurement of Ultra-short Laser Pulses, (Kluwer Academic Publishers, 2004.
18. D. J. Kane, G. Rodriguez, A. J. Taylor, and T. S. Clement, Simultaneous measurement of two ultrashort laser pulses from a single spectrogram in a single shot, J. Opt. Soc. Am., 935-943 (1997.
19. D. J. Kane, Recent progress toward real-time measurement of ultrashort laser pulses, IEEE J. Quantum Electron. 421-431 (1999.
20. L. Cohen, Time-frequency analysis, (Prentice Hall PTR, 1995.
21. D. Keusters, H.-S. Tan, P. O'Shea, E. Zeek, R. Trebino, and W. S. Warren, relative-phase ambiguities in measurements of ultrashort pulses with well-separated multiple frequency components, J. Opt. Soc. Am. 2226-2237 (2003.
22. D. N. Fittinghoff, K. W. Delong, R. Trebino, and C. L. Ladera, Noise Sensitivity in Frequency-Resolved-Optical-Gating Measurements of Ultrashort Optical Pulses, J. Opt. Soc. Am., 1955-1967 (1995.
23. D. J. Kane, F. G. Omenetto, and A. J. Taylor, Convergence test for inversion of frequency-resolved optical gating spectrograms, 1216-1218 (2000.
24. A. S. L. Gomes, V. L. Silva, and J. R. Taylor, Direct measurement of nonlinear frequency chirp of Raman radiation in single-mode optical fibers using a spectral window method, J. Opt. Soc. Am. 373-379 (1988.
25. M. V. Schulmerich, K. A. Dooley, M. D. Morris, T. M. Vanasse and S. A. Gold-stein, (2006. J. Biomedical Optics 11
26. R. Trebino, K. W. Delong, D. N. Fittinghoff, J. N. Sweetser, M. A. Krumbügel, B. A. Richman, and D. J. Kane, Measuring ultrashort laser pulses in the time-frequency domain using frequency-resolved optical gating, Rev. Sci. Instrum. 3277-3295 (1997.
27. L. P. Barry, J. M. Dudley, P. G. Bollond, J. D. Harvey, and R. Leonhardt, Complete characterisation of pulse propagation in optical fibres using frequency-resolved optical gating, Electron. Lett., 2339-2340 (1996.
28. I. Kang and C. Dorrer, Measurements of gain and phase dynamics of semiconductor optical amplifiers using spectrograms, Optical Fiber Conference, (2004
29. S. Linden, J. Kuhl, and H. Giessen, Amplitude and phase characterization of weak blue ultrashort pulses by down-conversion, Opt. Lett., 569-571 (1999.
30. P. O'Shea, P. Kimmel, X. Gu, and R. Trebino, Highly-simplified device for ultra-short pulse measurement, Opt. Lett. 932-934 (2001.
31. C. Dorrer and I. Kang, Simultaneous temporal characterization of telecommunication optical pulses and modulators using spectrograms, Opt. Lett., 1315-1317 (2002.
32. C. Dorrer, Investigation of the spectrogram technique for the characterization of picosecond optical pulses, Optical Fiber Communication Conference, (2005.
33. C. Dorrer and I. Kang, Real-time implementation of linear spectrograms for the characterization of high bit-rate optical pulse trains, Photon. Technol. Lett. 858-860 (2004.
34. Leary, Julie A. "Mass spectrometry." World Book Multimedia Encyclopedia. 2004.
35. Sobel, Michael I. "Light." The University of Chicago Press. 1987.
36. Utzinger U, Richards-Kortum R: Fiber optic probes for biomedical optical spectroscopy.
37. J Biomed Opt 2003, 8:121-147Moffitt T P, Prahl S A: Sized-fiber reflectomery for measuring local optical properties.
38. U.S. Army Research Laboratory. "What is Laser Induced Breakdown Spectroscopy (LIBS)?" (Oct. 26, 2008 Laser Focus World. "LIBS leaves the lab for field work in industry and defense." 2001. (Nov. 5, 2008)
39. Raman Spectroscopy for Homeland Security Applications J International Jounal of Spectroscopy % V 2012 C. Eliasson, N. A. Macleod and P. Matousek (2007.
40. "Non-invasive Detection of Concealed Liquid Explosives using Laser Spectroscopy". Analytical Chemistry 79 (21): 8185
41. C. Eliasson, N. A. Macleod and P. Matousek (2007. "Non-invasive Detection of Concealed Liquid Explosives using Laser Spectroscopy". Analytical Chemistry 79 (21): 8185-8189. doi:10.1021/ac071383n. PMID 17880183.
42. A Mogilevsky, Gregory, A Borland, Laura, A Brickhouse, Mark A Fountain III, Augustus W. R 10.1155/2012/808079 D 2012 Anita Mahadevan-Jansen and Rebecca R. Richards-Kortum
43. Raman spectroscopy for the detection of cancers and precancers", J. Biomed. Opt. 1(1), 31—
44. Biotags and Biomarkers: Gordon et al., J. Med. Chem., (1994), 37: 1385; U.S. Pat. No. 5,539,083 (nucleic acid libraries, peptide nucleic acid libraries)
45. Liang et al., Science (1996), 274: 1520-1522 (antibody libraries); and U.S. Pat. No. 5,593,853.
46. Baum, C & E N (Jan. 18, 1993), 33 Benzodiazepines); U.S. Pat. No. 5,569,588 (isoprenoids);
47. U.S. Pat. No. 5,549,974 (thiazolidinones and metathiazanones); U.S. Pat. No. 5,525,735 (pyrrolidines and U.S. Pat. No. 5,519,134 (morpholinos); U.S. Pat. Nos. 5,506, 337; and 5,288,514 Benzodiazepines.
48. Pharmaceutical counterfeiting Anil K. Deisingh Received 21 May 2004, Accepted 25 Nov. 2004 DOI: 10.1039/b407759h.
Physics and Matter
1. Weigel, M. and F. Weber. 1985. Ground-state Properties of Nuclear Matter using the Approximations of the Green's Function Theory. Phys. Rev. C 62: 2141.
2. Negreiros, R. and F. Weber. 2008. Thermal Properties of Neutron Stars in the Framework of Density-Dependent Nuclear Field Theory In Proceedings of Science.
3. Negreiros, R., P. Rosenfield and F. Weber. 2008. Neutron Star Interiors and the Equation of State of Superdense Matter. Astrophysics and Space Library 357: 213-245.
4. Ippolito, N., M. Ruggieri, A. Sedrakian, D. Rischke and F. Weber. 2008. Equilibrium Sequences of Non-Rotating and Rapidly Rotating Crystalline Color Super-conducting Hybrid Stars. Phys. Rev. D 77: 023004.
5. Klaehn, T., D. Blaschke and F. Weber. 2008. Constraints on the High-Density Nuclear Equation of State from Neutron Star Observables. To appear in Int. J. Mod. Physics.
6. Klaehn, S., D. Blaschke and F. Weber. 2008. Compact Star Constraints on the High-Density Equation of State. In Compressed Baryonic Matter (in press), edited by New York: Springer.
7. Torres I. Cuadrat, A., R. Negreiros, P. Rosenfield and F. Weber. 2007. Neutron Star Interiors and the Equation of State of Ultra-dense Matter. In, 515. AIP Conference Proceedings.
8. Suh, I., K. Otsuki, N. Lan, G. Mathews and F. Weber. 2007. Evidence for white dwarfs with Strange Matter Cores. Int. Journal of Mod. Phys. D (in press.
9. Weber, F., M. Meixner, R. Negreiros and M. Malheiro. 2007. Ultra-dense Neutron Star Matter, Strange Quark Matter, and the Nuclear Equation of State. Int. Jour-nal of Modern Physics E 16: 1165.
10. Negreiros, R., P. Rosenfield and F. Weber. 2007. Pulsars as Astrophysical Laboratories for Nuclear and Particle Physics. Progress in Nuclear and Particle Physics 59: 94.
11. Negreiros, R., P. Rosenfield and F. Weber. 2007. Rotating Neutron Stars. Europe-a Journal of Physics A33, No. 2: 1363.
12. Torres i Cuadrat, A., A. Ho, P. Rosenfield and F. Weber. 2006. Strangeness in Compact Star. In, 234. Proceedings of Sciences.
13. Page, D., U. Geppert and F. Weber. 2006. Neutron Star Cooling. Nuclear Physics A 777: 492.

14. Ho, A., T. Klaehn and F. Weber. 2006. Constraints of the high-density nuclear equation of state from the phenomenology of compact stars and heavy-ion collisions. Phys. Rev. C 74: 035802.
15. Otsuki, K., I. Suh, B. O'Gorman, N. Lan, W. Zech, G. Mathews and F. Weber. 2006. Analysis of White Dwarfs with Strange-Matter Cores. J. Phys. G: Nucl. Part. Phys 32: 1.
16. Negreiros, R., A. Ho, P. Rosenfield and F. Weber. 2006. Strangeness in Neutron Stars. Int. Journal of Modern Physics D (in press.
17. Torres i Cuadrat, A. and F. Weber. 2005. Compact Star Properties revised with Color Superconducting Phases of Quark Matter: Implications on Rotation and Emission. In 29th International Cosmic Ray Conference. Proceedings of the 29th International Cosmic Ray Conference, Aug. 3-10, 2005, Pune, India.
18. Weber, F. 2005. Strange Quark Matter and Compact Stars. Prog. Part. Nucl. Phys 54: 193-288.
19. Weber, F. 2004. The Equation of State of Neutron Star Matter. In International Workshop on Astronomy and Relativistic Astrophysics, Olinda, Brazil, 12-16 Oct. 2003, 1275-1288. International Journal of Modern Physics D.
20. Weber, F. 2004. Neutron Stars and Quark Stars. In KIAS-APCTP International Symposium in Astro-Hadron Physics, Nov. 10-14, 2003, Institute for Advanced Study, Seoul, Korea, 128-143. Singapore: World Scientific.
21. O'Gorman, B., G. Mathews and F. Weber. 2003. Evidence for White Dwarfs with Strange-Matter Cores. In American Astrophysical Society Meeting 199. Bibliography code: 2001AAS . . . 199.27010.
22. Weber, F. 2003. Nuclear and High-Energy Astrophysics. In Proceedings of the International Hadron Physics School 2002, 73-134. Singapore: World Scientific, ISBN 981-238-192-9.
23. Weber, F. 2003. Quark Matter in Compact Stars. Nucl. Phys. A 721: 1032c-1040c.
24. Bastrukov, S., J. Yang, D. Podgainy and F. Weber. 2003. Signatures of Field-induced Spin Polarization of Neutron Star Matter in Seismic Vibrations of Paramagnetic Neutron Stars. J. Phys. G: Nucl. Part. Phys 29: 683-702.
25. Burgio, G., H. Schulze and F. Weber. 2003. On the Maximum Rotational Frequency of Neutron and Hybrid Stars. Astronomy & Astrophysics 408: 675-682.
26. Glendenning, N. and F. Weber. 2002. Spin Clustering of Accreting X-ray Neutron Stars as Possible Evidence of Quark Matter. In International Nuclear Physics Conference 2001, 30 Jul. to 3 Aug. 2001, Berkeley, Calif., USA, 470-474. AIP.
27. Bastrukov, S., D. Podgainy, J. Yang and F. Weber. 2002. Magneto torsional pulsations of magnetars. Journal of Italian Astronomical Society 73: 522-533.
28. Bastrukov, S., D. Podgainy, J. Yang and F. Weber. 2002. Electromagnetic activity of pulsating paramagnetic neutron stars. JETP 95: 789-799.
29. Weber, F., G. Wolf and C. Chiba. 2002. Neutron star properties with in-medium vector mesons. nucl-th/0202071: 1-13.
30. Weber, F. 2002. From Neutron Stars to Strange Stars. Published in eConf C010815 ISBN 87: 17-28.
31. Bastrukov, S., J. Yang, D. Podgainy and F. Weber. 2001. Magnetoelastic Pulsations of Neutron Stars. In AIP Proceedings of the First KIAS Conference on Explosive Phenomena in Astrophysical Compact Objects, Seoul, Korea, May 22-26, 2000, 197-210. AIP.
32. Glendenning, N. and F. Weber. 2001. Phase Transition and Spin Clustering of Neutron Stars in X-ray Binaries. Astrophysical Journal 559: L119.
33. Weber, F. 2001. Strangeness in Neutron Stars. J. Phys. G: Nucl. Part. Phys 27: 465-474.
34. Glendenning, N. and F. Weber. 2001. Signal of Quark Deconfinement in Millisecond Pulsars and Reconfinement in Accreting X-ray Neutron Stars. In Lecture Notes in Physics, edited by, 305.
35. Weber, F. 2000. Signal of Quark Deconfinement in Neutron Stars. In Proceedings of the International Workshop on Understanding of Deconfinement in QCD, Trento, Italy Mar. 1-13, 1999, ed. by D. Blaschke, F. Karsch and C. D. Roberts, 334. Singapore: World Scientific.
36. Weber, F. 1999. Exotica in Neutron Stars. In Topical Workshop EOS 2000, Gesell-schaft für Schwerionenforschung (GSI), organized by P. Braun-Munzinger, J. Knoll, H. Oeschler, W. Reisdorf, P. Senger Coordinator), R. Stock, and H. Stroebele, Darmstadt, Germany, Feb. 20-23, 1999. Darmstadt, Germany: GSI.
37. Weber, F. 1999. From Boson Condensation to Quark Deconfinement: The Many Faces of Neutron Star Interiors. Acta Physica Polonica B 30: 3149.
38. Podgainy, D., S. Bastrukov and F. Weber. 1999. On the Stability of Global Non-Radial Pulsations of Neutron Stars. J. Phys. G: Nucl. Part. Phys 25: 107.
39. Molodtsova, I., V. Papoyan, D. Podgainy, S. Bastrukov and F. Weber. 1999. Elastodynamic Properties of Nuclear Matter from the Observed Activity of Neutron Stars. Phys. Nucl. & Part 30: 436.
40. Grigorian, H., B. Hermann and F. Weber. 1999. Quark-Hadron Phase Transition in Neutron Stars. Phys. Part. & Nucl 30: 156.
41. Sedrakian, A., C. Schaab, F. Weber and M. Weigel. 1999. Impact of Internal Heating on the Thermal Evolution of Neutron Stars. Astronomy & Astrophysics 346: 465.
42. Strobel, K., F. Weber and M. Weigel. 1999. Symmetric and Asymmetric Nuclear Matter in the Thomas-Fermi Model at Finite Temperatures. Z. Naturforsch 54A: 83.
43. Huber, H., M. Weigel and F. Weber. 1999. Compatibility of Neutron Star Masses and Hyperon Coupling Constants. Z. Naturforsch 54A: 77.
44. Weber, F. 1999. Quark Matter in Neutron Stars. J. Phys. G: Nucl. Part. Phys 25: R195.
45. Weber, F. 1999. Pulsars as Astrophysical Laboratories for Nuclear and Particle Physics; Studies in High Energy Physics, Cosmology and Gravitation. Bristol, Great Britain: Institute of Physics Publishing Corporation, 682 pages.
46. Weber, F., N. Glendenning and S. Pei. 1998. Signal for the Quark-Hadron Phase Transition in Rotating Hybrid Stars. In Proceedings of the 3rd International Conference on Physics and Astrophysics of Quark-Gluon Plasma, Jaipur, India, ed. by B. C. Sinha, D. K. Srivastava, Y. P. Viyogi, 237. New Delhi: Narosa Publishing House.
47. Weber, F. 1998. Neutron Stars. In Int. Astrophysics Conference, Big Sky, Mont., Laser Optics
1. Bibcode:2006ApSpe . . . 60.1341M. doi:10.1366/000372006778999102. PMID 17132454. Hecht, Jeff. "Optics: Light for a New Age." Charles Scribner's Sons. 1987.
2. Hering, Peter, J. P. Lay and Sandra Story. "Laser in Environmental and Life Sciences." Springer. 2004.

3. Brancaleon L, Durkin A J, Tu J H, Menaker G, Fallon J D, Kollias N: In vivo fluorescence spectroscopy of non-melanoma skin cancer. Photochem Phobiol 2001,
4. R. Trebino, Frequency-Resolved Optical Gating: The Measurement of Ultrashort Laser Pulses, (Kluwer Academic Publishers, 2004.
5. D. J. Kane, G. Rodriguez, A. J. Taylor, and T. S. Clement, Simultaneous measurement of two ultrashort laser pulses from a single spectrogram in a single shot, J. Opt. Soc. Am., 935-943 (1997.
6. D. J. Kane, Recent progress toward real-time measurement of ultrashort laser pulses, IEEE J. Quantum Electron. 421-431 (1999.
7. L. Cohen, Time-frequency analysis, (Prentice Hall PTR, 1995.
8. D. Keusters, H.-S. Tan, P. O'Shea, E. Zeek, R. Trebino, and W. S. Warren, Relative-phase ambiguities in measurements of ultrashort pulses with well-separated multiple frequency components, J. Opt. Soc. Am. 2226-2237 (2003.
9. D. N. Fittinghoff, K. W. Delong, R. Trebino, and C. L. Ladera, Noise Sensitivity in Frequency-Resolved-Optical-Gating Measurements of Ultrashort Optical Pulses, J. Opt. Soc. Am., 1955-1967 (1995.
10. D. J. Kane, F. G. Omenetto, and A. J. Taylor, Convergence test for inversion of frequency-resolved optical gating spectrograms, 1216-1218 (2000.
11. A. S. L. Gomes, V. L. Silva, and J. R. Taylor, Direct measurement of nonlinear frequency chirp of Raman radiation in single-mode optical fibers using a spectral window method, J. Opt. Soc. Am. 373-379 (1988.
12. M. V. Schulmerich, K. A. Dooley, M. D. Morris, T. M. Vanasse and S. A. Goldstein, (2006. J. Biomedical Optics 11
13. R. Trebino, K. W. Delong, D. N. Fittinghoff, J. N. Sweetser, M. A. Krumbügel, B. A. Richman, and D. J. Kane, Measuring ultrashort laser pulses in the time-frequency domain using frequency-resolved optical gating, Rev. Sci. Instrum. 3277-3295 (1997.
14. L. P. Barry, J. M. Dudley, P. G. Bollond, J. D. Harvey, and R. Leonhardt, Complete characterisation of pulse propagation in optical fibres using frequency-resolved optical gating, Electron. Lett., 2339-2340 (1996.
15. I. Kang and C. Dorrer, Measurements of gain and phase dynamics of semi-conductor optical amplifiers using spectrograms, Optical Fiber Conference, (2004
16. S. Linden, J. Kuhl, and H. Giessen, Amplitude and phase characterization of weak blue ultrashort pulses by down-conversion, Opt. Lett., 569-571 (1999.
17. P. O'Shea, P. Kimmel, X. Gu, and R. Trebino, Highly-simplified device for ultrashort pulse measurement, Opt. Lett. 932-934 (2001.
18. C. Dorrer and I. Kang, Simultaneous temporal characterization of telecommunication optical pulses and modulators using spectrograms, Opt. Lett., 1315-1317 (2002.
19. C. Dorrer, Investigation of the spectrogram technique for the characterization of picosecond optical pulses, Optical Fiber Communication Conference, (2005.
20. C. Dorrer and I. Kang, Real-time implementation of linear spectrograms for the characterization of high bit-rate optical pulse trains, Photon. Technol. Lett. 858-860 (2004.
21. Leary, Julie A. "Mass spectrometry." World Book Multimedia Encyclopedia. 2004.
22. Sobel, Michael I. "Light." The University of Chicago Press. 1987.
23. Utzinger U, Richards-Kortum R: Fiber optic probes for biomedical optical spectroscopy J Biomed Opt 2003, 8:121-147Moffitt T P, Prahl S A: Sized-fiber reflectomery for measuring local optical properties.
23. U.S. Army Research Laboratory. "What is Laser Induced Breakdown Spectroscopy (LIBS)?" (Oct. 26, 2008 Laser Focus World. "LIBS leaves the lab for field work in industry and defense." 2001. (Nov. 5, 2008)
24. Raman Spectroscopy for Homeland Security Applications J International Journal of Spectroscopy % V 2012 C. Eliasson, N. A. Macleod and P. Matousek (2007.
25. "Non-invasive Detection of Concealed Liquid Explosives using Laser Spectroscopy". Analytical Chemistry 79 (21): 8185
26. C. Eliasson, N. A. Macleod and P. Matousek (2007. "Non-invasive Detection of Concealed Liquid Explosives using Laser Spectroscopy". Analytical Chemistry 79 (21): 8185-8189. doi:10.1021/ac071383n. PMID 17880183. A Mogilevsky, Gregory, A Borland, Laura, A Brickhouse, Mark A Fountain III, Augustus W. R 10.1155/2012/808079 D 2012
27. Anita Mahadevan-Jansen and Rebecca R. Richards-Kortum Raman spectroscopy for the detection of cancers and precancers 28.
Quantum Computing
1. David J. Wineland National Institute of Standards and Technology, Boulder, Colo. 80303 "12-qubits Reached In Quantum Information Quest." Science Daily, May 2006. http://www.sciencedaily.com/releases/2006/05/060508164700.htm
2. Aaronson, Scott. "Shtetl-Optimized." Apr. 10, 2007. http://scottaaronson.com/blog
3. Bone, Simone and Matias Castro. "A Brief History of Quantum Computing." Imperial College, London, Department of Computing. 1997.
4. Boyle, Alan. "A quantum leap in computing." MSNBC, May 18, 2000. http://www.msnbc.msn.com/id/3077363
5. "Center for Extreme Quantum Information Theory (xQIT), MIT." TechNews, March 2007. http://www.technologynewsdaily.com/node/6280
6. Centre for Quantum Computer Technology http://www.q-caustralia.org/Cory, D. G., et al. "Experimental Quantum Error Correction." American Physical Society, Physical Review Online Archive, September 1998. http://prola.aps.org/abstract/PRL/v81/i10/p2152_1
7. Grover, Lov K. "Quantum Computing." The Sciences, July/August 1999. http://cryptome.org/qc-grover.htm
8. Hogg, Tad. "An Overview of Quantum Computing." Quantum Computing and Phase Transitions in Combinatorial Search. Journal of Artificial Intelligence Research, 4, 91-128 (1996. http://www.cs.cmu.edu/afs/cs/project/jair/pub/volume4/hogg96a-html/node6.html
9. "IBM's Test-Tube Quantum Computer Makes History." IBM Research, Dec. 19, 2001. http://domino.watson.ibm.com/comm/pr.nsf/pages/news.20011219_quantum.html Institute for Quantum Computing. http://www.iqc.ca
10. Jonietz, Erika. "Quantum Calculation." Technology Review, July 2005. http://www.technologyreview.com/Infotech/14591
11. Maney, Kevin. "Beyond the P C: Atomic Q C." USA Today. http://www.amd1.com/quantum_computers.html
12. "Quantum Computing." Stanford Encyclopedia of Philosophy, Feb. 26, 2007. http://plato.stanford.edu/entries/qt-quantcomp Qubit.org http://www.qubit.org
13. Dimonite, Tom. "Flat 'ion trap' holds quantum computing promise." NewScientistTech, July 2006. http://www.newscientisttech.com/article/dn9502-flat-ion-trap-holds-quantum-computing-promise.html
14. Vance, Ashlee. "D-Wave qubits in the era of Quantum Computing." The Register, Feb. 13, 2007. http://www.theregister.co.uk/2007/02/13/dwave quantum.

Quantum Encryption
1. Wehner, Stephanie; Schaffner, Christian; Terhal, Barbara M. (2008. "Cryptography from Noisy Storage". Physical Review Letters (APS 100 (22): 220502. arXiv:0711.2895. Bibcode:2008PhRvL.100v0502W.
2. doi:10.1103/PhysRevLett.100.220502. PMID 18643410. A full version is available at arXiv:0711.2895.
3. Koenig, Robert; Wehner, Stephanie; Wullschleger, Juerg. "Unconditional security from noisy quantum storage". A full version is available at arXiv:0906.1030.
4. Cachin, Christian; Crépeau, Claude; Marcil, Julien (1998. "Oblivious Transfer with a Memory-Bounded Receiver". FOCS 1998. IEEE. pp. 493-502.
5. Dziembowski, Stefan; Ueli, Maurer (2004. "On Generating the Initial Key in the Bounded-Storage Model".
6. Chandran, Nishanth; Moriarty, Ryan; Goyal, Vipul; Ostrovsky, Rafail (2009. Position-Based Cryptography. A full version is available at IACR eprint:2009/364. U.S. Pat. No. 7,075,438, issued 2006 Jul. 11
7. Kent, Adrian; Munro, Bill; Spiller, Tim (2010. "Quantum Tagging with Crypto-graphically Secure Tags". A full version is available at arXiv:1008.2147.
8. Lau, Hoi-Kwan; Lo, Hoi-Kwong (2010. "Insecurity of position-based quantum-cryptography protocols against entanglement attacks". Physical Review A (APS 83: 012322. arXiv:1009.2256. doi:10.1103/PhysRevA.83.012322.
9. Malaney, Robert A. (2010. "Location-dependent communications using quantum entanglement". Physical Review A 81: 042319. doi:10.1103/PhysRevA.81.042319.
10. Buhrman, Harry; Chandran, Nishanth; Fehr, Serge; Gelles, Ran; Goyal, Vipul; Os-trovsky, Rafail; Schaffner, Christian (2010. "Position-Based Quantum Cryptography: Impossibility and Constructions".
11. Bernstein, Daniel J.; Buchmann, Johannes; Dahmen, Erik, eds. (2009. Post-quantum cryptography. Springer. ISBN 978-3-540-88701-0.

Chemistry, BioChemistry, Biomarkers, Biotags
1. Dale Shellhamer, Ph.D., and his team published "Reaction of Chlorosulfonyl Isocyanate With Fluorosubstituted Alkenes: Evidence for a Concerted Pathway" in the Journal of Organic Chemistry and "Reaction of Halogens and Interhalogens With 1,1,2-Trifluorobut 1-En-4-O1 and 3-Butene-1-01: A Study on the Rearrangement of Trifluorosubstituted 3-membered Halonium Ions" in Trends in Organic Chemistry.
2. "Addition Reactions of Electronegative Alkoxyxenon Fluorides with Alkenes," M. L. Druelinger, D. F. Shellhamer, R. D. Chapman, S. A. Shackelford, M. E. Reiner, S. L. Carter, R. P. Callahan and C. R. Youngstrom, Journal of the Chemical Society, London, Perkin Transactions 2, 787, 1997.
3. "The Fluorination of Cyclopentadiene and 3,4-Epoxycyclopentene," D. F. Shellhamer, M. C. Chiaco, K. M. Gallego, W. S. C. Low, B. Carter, V. L. Heasley, and R. D. Chapman, Journal of Fluorine Chemistry, 72, 83, 1995.
4. Reaction of Alkylhypochlorites and Xenon Difluoride with Cyclohexene," D. F. Shellhamer, M. J. Homey, A. L. Toth and V. L. Heasley, Tetrahedron Letters, 33, 6903, 1992.
5. "The Regioselectivity in the Addition of Alkoxyxenon Fluorides," D. F. Shellhamer, S. L. Carter, R. H. Dunham, S. N. Graham, V. L. Heasley, R. D. Chap-man and M. L. Druelinger, Journal of the Chemical Society, London, Perkin Transactions 2, 159, 1989 and references therein.
6. "Radical Additions of Xenon Difluoride to cis- and trans-1-Phenylpropenes: Comparison with Trichloroamine and Iodobenzene Dichloride," D. F. Shellhamer, M. L. Ragains, B. T. Gipe, V. L. Heasley and G. E. Heasley, The Journal of Fluorine Chemistry, 20, 13, "Reaction of Aminosulfur Trifluorides with Alcohols: Inversion vs. Retention", D. F. Shellhamer, A. A. Briggs, B. M. Miller, J. M. Prince, D. H. Scott and V. L. Heasley, Journal of the Chemical Society, London, Perkin Transactions 2, 973, 1996.
7. "Reaction of Diethylaminosulfur Trifluoride with Diols", D. F. Shellhamer, D. T. Anstine, K. M. Gallego, B. R. Ganesh, A. A. Hanson, K. A. Hanson, R. D. Henderson, J. M. Prince and V. L. Heasley, Journal of the Chemical Society, London, Perkin Transactions 2, 861, 1995.
8. The Fluorination of Cyclopentadiene and Epoxycyclopentene", D. F. Shellhamer, M. C. Chiaco, K. M. Gallego, W. S. C. Low, B. Carter, V. L. Heasley and R. D. Chapman. Journal of Fluorine Chemistry, 72, 83, 1995.
9. Facile Addition of Poorly Nucleophilic Alcohols to Unactivated Alkenes", D. F. Shellhamer, R. P. Callahan, M. L. Druelinger, R. D. Chapman, and V. L. Heasley. Synthesis, 1997, 9, 1056.
10. "The Chemistry of Interhalogen Monofluorides," Dale F. Shellhamer* and Victor L. Heasley, Advances in Organic Synthesis, 2006, Vol. 2, Bentham Science Publishers, p. 43.
11. Symmetry of Chloronium Ions from Ionic Reactions of Chlorine, Chlorine Monofluoride Gas and Chlorine Monofluoride Complex with Terminal Alkenes," D. F. Shellhamer, P. K. Titterington*, V. L. Heasley. J. Fluorine Chem., 124, 17, 2003.
12. Generating Interhalogen Fluorides under Mild Conditions: A Comparison of Sluggish and Reactive Interhalogen Fluorides," D. F. Shellhamer, M. J. Homey, B. J. Pettus, T. L. Pettus, J. M. Stringer, and V. L. Heasley. J. Org. Chem., 64, 1094, 1999.
13. A Mild Method for introducing iodine Monofluoride into Alkenes and Iodination of Aromatics Using Xenon Difluoride," D. F. Shellhamer, B. C. Jones, B. J. Pettus, T. L. Pettus, J. M. Stringer, V. L. Heasley. J. Fluorine. Chem., 88, 37, 1998.
14. "Generating Interhalogen Fluorides," D. F. Shellhamer, B. C. Jones, B. J. Pettus, T. L. Pettus, J. M. Stringer, V. L. Heasley, Robert G. Syvret and John M. Dobrolsky, Jr. Oral presentation at The 13th Winter Fluorine Conference at St. Petersburg Beach, F L on Jan. 23, 1997.
15. Reaction of Alkylhypohalites and Xenon Difluoride with Cyclohexene," D. F. Shellhamer, M. J. Homey, A. L. Toth and V. L. Heasley, Tetrahedron Letters, 33, 6903, 1992.
16. Oral presentation: "A Mechanistic Study on the Generation of Interhalogen Fluorides: A Search for Reaction Intermediates," B. J. Pettus and D. F. Shellhamer. Presented by B. J. Pettus at the 1997 Southern California Undergraduate Research Conference in Chemistry and Biochemistry on Apr. 26, 1997 at California State University, Northridge, C A.
17. "Addition of Open-Ion Electrophiles to Monofluoroterminal Alkenes and Hydrocarbon Alkenes" D. F. Shellhamer, H. K. Forberg, M. P. Herrick, S. J. Rodriguez, S. Sanabria, N. N. Trager and V. L. Heasley, Trends in Organic Chemistry, 2008, in press.
18. "Rearrangement of 3-Membered 1,1,2-Trifluorobromonium and Iodonium Ions and Comparison of Trifluorochloronium to Fluorocarbenium Ions" D. F. Shellhamer, K. J. Davenport, H. K. Forberg, M. P. Herrick, R. N. Jones, S. J. Rodriguez, S. Sanabria, N. N. Trager, R. J. Weiss, V. L. Heasley and J. A. Boatz, J. Org. Chem. 2008, 73, 4532.

19. "Correlation of Calculated Halonium Ion Structures with Experimental Product Distributions from Terminal Alkenes: The Effect of Electron-Withdrawing Fluorine Substituents on the Structure and Charge Localization of Halonium Ions," D. F. Shellhamer, D. C. Gleason*, V. L. Heasley, and J. J. Lehman. Tetrahedron, 2006, 62, 11608.

20. "Ionic Reaction of Halogens with Terminal Alkenes: The Effect of Electron-Withdrawing Fluorine Substituents on the Bonding of Halonium Ions," D. F. Shellhamer, J. L. Allen*, R. D. Allen*, D. C. Gleason*, C. O'Neil Schlosser*, B. J. Powers*, J. W. Probst*, M. C. Rhodes*, A. J. Ryan*, P. K. Titterington*, G. G. Vaughan* and V. L. Heasley. J. Org. Chem., 68, 3932, 2003.

21. "Symmetry of Chloronium Ions from Ionic Reactions of Chlorine, Chlorine Mono-fluoride Gas and Chlorine Monofluoride Complex with Terminal Alkenes," D. F. Shellhamer, P. K. Titterington*, V. L. Heasley. J. Fluorine Chem., 124, 17, 2003.

22. "Comparison of the Electrophilic and Free-Radical and 1,3-Butadien," D. F. Shellhamer, D. C. Gleason*, G. G. Vaughan*, A. J. Ryan*, P. K. Titterington*, V. L. Heasley and J. J. Lehman. J. Fluorine Chem., 123, 171, 2003.

23. "The Chemistry of Interhalogen Monofluorides," Dale F. Shellhamer and Victor L. Heasley in Advances in Organic Synthesis, Vol. 2, 2006, pg. 43. Bentham Science Publishers, the Netherlands. ISBN: 90-77527-08-7.

24. "Is there a Time and Place for Radiopaque Fluorocarbons," D. M. Long, C. B. Higgins, R. F. Mattrey, R. M. Mitten, F. K. Multer, C. M. Sharts and D. F. Shellhamer in Preparation, Properties, and Industrial Applications of Organofluorine Compounds, 1982, pg. 139, Ellis Harwood Limited, England. ISBN: 0-85312-276-8.

25. "Kinetic Studies on the Reaction of Chlorosulfonyl Isocyanate with Monofluoroalkenes: Experimental Evidence for Both Stepwise and Concerted Mechanisms and a Pre-equilibrium Complex on the Reaction Pathway", Dale F. Shellhamer*, Summer A. Bunting, Kelli R. Hickle, Parker C. Horn, Jacob C Milligan, Danielle E. Shipowick, Lincoln B. Smith, David J. Vandenbroek, Marc C. Perry, and Jerry A Boatzt, Journal of Organic Chemistry, 2013, 78, 246-252

26. "Kinetic Studies on the Reaction of Chlorosulfonyl Isocyanate with Monofluoroalkenes: Experimental Evidence for Both Stepwise and Concerted Mechanisms and a Pre-equilibrium Complex on the Reaction Pathway", Dale F. Shellhamer*, Summer A. Bunting, Kelli R. Hickle, Parker C. Horn, Jacob C Milligan, Danielle E. Shipowick, Lincoln B. Smith, David J. Vandenbroek, Marc C. Perry, and Jerry A Boatzt, Journal of Organic Chemistry, 2013, 78, 246-252

27. "Reaction of chlorosulfonyl isocyanate with fluorosubstituted alkenes: Evidence for a concerted pathway" Shellhamer, Dale F.; Davenport*, Kevyn J.; Hassler*, Danielle M.; Hickle*, Kelli R.; Thorpe*, Jacob J.; Vandenbroek*, David J.; Heasley, Victor L.; Boatz, Jerry A.; Reingold, Arnold L. and Moore, Curtis E., Journal of Organic Chemistry, 2010, 75, 7913.

28. "Synthesis of a New Humic Acid Model, 2,4,6,6-Tetrachloro-2-methylcyclohex-4-ene-1,3-dione and Investigation of its Reactions with Monochloramine in Ether and in Methanol" Heasley, Victor L., Mitrovich, Kristin M., Sator Lisa C., Fisher, Audra M., Kerk, Amber R. E. and Shellhamer, Dale F., Research Journal of Chemistry and Environment, 2010, 14(4), 52.

29. "Reaction of halogens and interhalogens with 1,1,2-trifluorobut-1-en-4-ol and 3-butene-1-ol: A study on the rearrangement of trifluorosubstituted 3-membered haloniumions" Shellhamer, Dale F.; Davenport*, Kevyn J.; Jones*, Rachel N.; Thorpe*, Jacob J.; Weiss*, Ryan J. and Heasley, Victor L., Trends in Organic Chemistry, 2010, 14, 73-76.

30. "Addition of Open-Ion Electrophiles to Monofluoroterminal Alkenes and Hydro-carbon Alkenes" D. F. Shellhamer, H. K. Forberg, M. P. Herrick, S. J. Rodriguez, S. Sanabria, N. N. Trager and V. L. Heasley, Trends in Organic Chemistry, 2008, 12, 39. Chemistry Biochemistry 1. C. A. Ng, W. Zhao, J. Dang, M. Bergdahl, F. Separovic, R. T. C. Brownlee, and R. P. Metzger, "The Conformation of Acetylated Virginiamycin M1 and Virginiamycin M1 in Explicit Solvents." Biochim. Biophys. Acta 1774, 2006 610-618.

2. R. P. Metzger, "Thoughts on the teaching of metabolism," Biochem. Molec. Bio. 34, 2006 78-87.

3. J. Dang, R. P. Metzger, R. T. C. Brownlee, C. A. Ng, M. Bergdahl and F. Separovic, "The conformational flexibility of the antibiotic Virginiamycin M1," Eur. Biophys. J. 34, 2005 383-388.

4. J. L. Lord, A. de Peyster, P. J. E. Quintana, and R. P. Metzger, "Cytotoxicity of Xanthopterin and Isoxanthopterin in MCF-7 Cells," Cancer Lett. 222, 2005 119-124.

5. J. Dang, F. Separovic, B. M. Bergdahl, R. T. C. Brownlee and R. P. Metzger, "Solvent Affects the Conformation of Virginiamycin M1 (Pristinamycin IIA, Streptogramin A)," Org. Biomol. Chem. 2, 2004 2919-2924.

6. J. Dang; B. M. Bergdahl; F. Separovic; R. T. C. Brownlee; R. P. Metzger, "Virginiamycin M1 Conformation in Solution Differs From the Form Bound to the 505 Ribosome and to Streptogramin Acetyltransferase," Aust. J. Chem. 2004 415.

7. G. Herzberg, Molecular Spectra and Molecular Structure: I Diatomic Molecules, Prentice Hall Inc., New York, 1939.

8. G. Herzberg, Molecular Spectra and Molecular Structure: II Infrared and Raman Spectra of Polyatomic Molecules, D. Van Nostrand Co. Inc., New York, 1945.

9. G. Herzberg, Molecular Spectra and Molecular Structure: III Electronic Spectra and Electronic Structure of Polyatomic Molecules, D. Van Nostrand Co. Inc., New York, 1966.

10. B. Stoicheff, Gerhard Herzberg: An Illustrious Life in Science, NRC Press, Ottawa, Ont. Canada, 2002, 468 pp.

11. G. Herzberg, E. Teller, Z. Phys. Chem. B21 (1933 410.

The invention claimed is:

1. A method for generating a spectrum of emissions from a sample that has been irradiated comprising:
  a providing a laser including a quantum well, the quantum well comprising an active region;
  b initiating an electron flow to an N-P semiconductor in said laser;
  c selectively providing the electron flow at a first, low energy at a level to produce a sublasering energy level, whereby a transmission package is created in said active region;
  d coupling a trigger pulse to said N-P semiconductor to cause lasing to initiate transmission of the transmission package from said laser at a preselected time after initiation of electron flow from said source of electron flow;

e positioning a single fiber to carry the transmission package from the laser and to carry and couple a received emission package to a spectrometer;

f positioning a surface, the surface being at an end of the single fiber to transmit a transmission package and to receive an emission package from the sample; and g transmitting the transmission package for excitation of the sample, receive an emission package produced by the sample in response to the excitation, and coupling the emission package for measurement.

2. A method according to claim 1 comprising coupling the transmission package to the fiber via a Raman probe.

3. A method according to claim 2 further comprising aligning the fiber with said Raman probe and positioning the fiber between the Raman probe and the sample to focus the transmission package on the sample.

4. A method according to claim 2 comprising transmitting transmission packages from said Raman probe via a focal convergence field.

5. A method according to claim 4 comprising receiving the emission package from the sample via the focal convergence field.

6. A method according to claim 1 wherein forming the transmission package comprises performing sublasering in a quantum well comprising a separate confinement laser quantum well intermediate said n and p type layers in said NP semiconductor.

7. A method according to claim 1 further comprising irradiating a static sample once at a first time and measuring energy emitted by the sample at the first time and at at least a second time to provide a first result and a second result.

8. A method according to claim 1 further comprising agitating the static sample at a first time to provide an agitated sample and comparing a result from the agitated sample to a corresponding result from the static sample.

\* \* \* \* \*